United States Patent
Chen et al.

(10) Patent No.: US 10,061,052 B2
(45) Date of Patent: Aug. 28, 2018

(54) MODELING SUBTERRANEAN FLUID VISCOSITY

(71) Applicant: Halliburton Energy Services, Inc., Houston, TX (US)

(72) Inventors: Songhua Chen, Katy, TX (US); Wei Shao, Conroe, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 66 days.

(21) Appl. No.: 14/399,025

(22) PCT Filed: Dec. 12, 2013

(86) PCT No.: PCT/US2013/074810
§ 371 (c)(1),
(2) Date: Nov. 5, 2014

(87) PCT Pub. No.: WO2015/088543
PCT Pub. Date: Jun. 18, 2015

(65) Prior Publication Data
US 2016/0231451 A1    Aug. 11, 2016

(51) Int. Cl.
*G01V 3/32* (2006.01)
*G01N 24/08* (2006.01)

(52) U.S. Cl.
CPC ............. *G01V 3/32* (2013.01); *G01N 24/081* (2013.01)

(58) Field of Classification Search
CPC ........ G01V 3/32; G01N 24/081; G01R 33/50; G01R 33/5615
USPC .......................................................... 702/12
See application file for complete search history.

(56) References Cited

U.S. PATENT DOCUMENTS

| | | |
|---|---|---|
| 7,091,719 B2 | 8/2006 | Freedman |
| 7,309,983 B2 | 12/2007 | Freedman |
| 8,195,399 B2 | 6/2012 | Gladkikh et al. |
| 2003/0016013 A1* | 1/2003 | Kruspe .................... G01V 3/32 324/303 |
| 2003/0107374 A1 | 6/2003 | Chen et al. |

(Continued)

FOREIGN PATENT DOCUMENTS

| | | |
|---|---|---|
| EP | 1003053 | 5/2000 |
| WO | 2013023299 | 2/2013 |

OTHER PUBLICATIONS

Freedman, R. "A New NMR Method of Fluid Characterization in Reservoir Rocks: Experimental Confirmation and Simulation Results"., Dec. 2001 Spe Journal.*

(Continued)

*Primary Examiner* — Yoshihisa Ishizuka
(74) *Attorney, Agent, or Firm* — Benjamin Fite; Parker Justiss, P.C.

(57) ABSTRACT

Systems, methods, and software for modeling subterranean formation viscosity are described. In some aspects, a method of training a subterranean fluid viscosity model based on NMR data includes accessing multiple relaxation-time distributions generated from NMR measurements of a fluid, normalizing each relaxation-time distribution to a common normalizing value, computing parameters for a plurality of weighted radial basis functions from the normalized relaxation-time distributions, and producing a subterranean fluid viscosity model that includes the weighted radial basis functions and the computed parameters.

22 Claims, 21 Drawing Sheets

(56) References Cited

U.S. PATENT DOCUMENTS

| | | | |
|---|---|---|---|
| 2005/0242807 A1 | 11/2005 | Freedman | |
| 2006/0055403 A1 | 3/2006 | Freedman | |
| 2008/0036457 A1 | 2/2008 | Thern et al. | |
| 2008/0154509 A1* | 6/2008 | Heaton | G01V 11/00 702/7 |
| 2008/0206887 A1 | 8/2008 | Chen et al. | |
| 2009/0174402 A1 | 7/2009 | Rottengatter | |
| 2009/0292473 A1 | 11/2009 | Kruspe et al. | |
| 2010/0138157 A1 | 6/2010 | Sun et al. | |
| 2010/0271019 A1 | 10/2010 | Anand | |
| 2011/0025324 A1 | 2/2011 | Fransson et al. | |
| 2011/0234220 A1* | 9/2011 | Mitchell | G01N 24/081 324/303 |
| 2012/0065888 A1 | 3/2012 | Wu et al. | |
| 2013/0207814 A1* | 8/2013 | Tietjen | G01V 1/40 340/856.3 |
| 2013/0257424 A1* | 10/2013 | Holland | G01N 24/081 324/303 |

OTHER PUBLICATIONS

International Search Report and Written Opinion of the International Searching Authority issued in International Application No. PCT/US2013/074810 dated Sep. 12, 2014; 10 pages.

International Search Report and Written Opinion of the International Searching Authority issued in International Application No. PCT/US2013/074804 dated Sep. 12, 2014; 10 pages.

Abragam, "Principles of Nuclear Magnetism," ISBN-10: 019852014X, ISBN-13, 978-0198520146 (p. 300) 3 pages.

Anand et al, "Predicting Effective Permeability to Oil in Sandstone and Carbonate Reservoirs from Well Logging Data.", SPE 134011, Sep. 19-22, 2010, 19 pages.

Bloembergen et al., "Relaxation Effects in Nuclear Magnetic Resonance Absorption" Physical Review, Apr. 1, 1948, vol. 73, No. 7, pp. 679-712.

Bryan et al., "In-Situ Viscosity of Oil Sands Using Low-Field NMR", J. Can. Petro. Tech., vol. 44(9), Sep. 2005, pp. 23-29.

Bryan et al., "Oil-Viscosity Predictions from Low-Field NMR Measurements", SPE Reservoir Evaluation & Engineering, Feb. 2005, pp. 44-52.

Chen et al, "A New NMR T, Measurement Technique for Gas Shale, Heavy Oil, and Microporosity Characterizations," International Symposium of the Society of Core Analysts, Aug. 2012, 12 pages.

Chen et al., "Value of NMR Logging for Heavy Oil Characterization", World Heavy Oil Congress Paper 2008-353, Mar. 12, 2008, 16 pages.

Cheng et al., "Power-law Relationship between the Viscosity of Heavy Oils and NMR Relaxation", SPWLA 50th Annual Logging Symposium, Jun. 21-24, 2009, 7 pages.

Coates et al., "The MRIL* in Conoco 33-1, An Investigation of a New Magnetic Resonance Imaging Log", SPWLA 32nd Annual Logging Symposium, Jun. 16-19, 1991, 24 pages.

Gao et al, "New Method for Predicting Capillary Pressure Curves from NMR Data in Carbonate Rocks", SPWLA 52nd Annual Logging Symposium, May 14-18, 2011, 11 pages.

Kenyon et al, "A Three-Part Study of NMR Longitudinal Relaxation Properties of Water-Saturated Sandstones", SPE Formation Evaluation, Sep. 1988, 622-636.

Kleinberg et al., "NMR Properties of Reservoir Fluids", The Log Analyst, Nov.-Dec. 1996, pp. 20-32.

Kozeny, "Kozeny-Carman Equation", Wikipedia, last modified Apr. 20, 2013, 2 pages, retrieved from Internet at http://en.wikipedia.org/w/index.php?title=Kozeny-Carman_equation&oldid=551352710.

La Torraca et al., Low-Field NMR Determinations of the Properties of Heavy Oils and Water-in-Oil Emulsions; Magn. Reson. Img., vol. 16, No. 5-6, Published in 1998, pp. 659-662.

Orr, "Introduction to Radial Basis Function Networks," Apr. 1996, 67 pages.

Morriss et al., Hydrocarbon Saturation and Viscosity Estimation from NMR Logging in the Belridge Diatomite, SPWLA 35th Annual Logging Symposium, Jun. 19-22, 1994, 24 pages.

Nicot et al., "Improvement of Viscosity Prediction Using NMR Relaxation", SPWLA 48th Annual Logging Symposium, Jun. 3-6, 2007, 7 pages.

Orr, "Matlab Functions for Radial Basis Function Networks", Institute for Adaptive and Neural Computation Division of Informatics, Jul. 9, 1999, 69 pages.

Shafer et al, "Methods and Procedures for Calibrating NMR Log Derived Permeabilities," 11th Formation Evaluation Symposium of Japan, Oct. 5-6, 2005, 15 pages.

Worthington, "The Effect of Scale on the Petrophysical Estimation of Intergranular Permeability", Petrophysics, vol. 45, No. 1, Jan.-Feb. 2004, pp. 59-72.

Zhang et al., "Some Exceptions to Default NMR Rock and Fluid Properties", SPWLA 39th Annual Logging Symposium, May 26-29, 1998, 14 pages.

"Principal Component Analysis", Wikipedia, last modified Sep. 28, 2013, 19 pages, retrieved from internet at: http://en.wikipedia.org/wiki/Principal_component_analysis.

Shao et al., "Modeling Subterranean Formation Permeability," PCT International Application No. PCT/US2013/074804, filed Dec. 12, 2013, 49 pages.

Communication pursuant to article 94(3) epc issued in european application No. 13884958.3, Jun. 29. 2016.

Anand et al, "New methods for predicting properties of live oils from NMR," SPLWA 50th annual logging symposium, Jun. 24, 2009, <https://www.onepetro.org/download/conference-paper/SPWLA-2009-88680?id=conference-paper/SPWLA-2009-88680>.

* cited by examiner

MODELING SUBTERRANEAN FLUID VISCOSITY

CLAIM OF PRIORITY

This application is a U.S. National Stage of International Application No. PCT/US2013/74810, filed Dec. 12, 2013.

BACKGROUND

This specification relates to modeling subterranean fluid viscosity based on nuclear magnetic resonance (NMR) data associated with a subterranean region.

In the field of logging (e.g. wireline logging, logging while drilling (LWD) and measurement while drilling (MWD)), nuclear magnetic resonance (NMR) tools have been used to explore the subsurface based on the magnetic interactions with subsurface material. Some downhole NMR tools include a magnet assembly that produces a static magnetic field, and a coil assembly that generates radio frequency (RF) control signals and detects magnetic resonance phenomena in the subsurface material. Properties of the subsurface material can be identified from the detected phenomena.

DETAILED DESCRIPTION

Figure 1A:
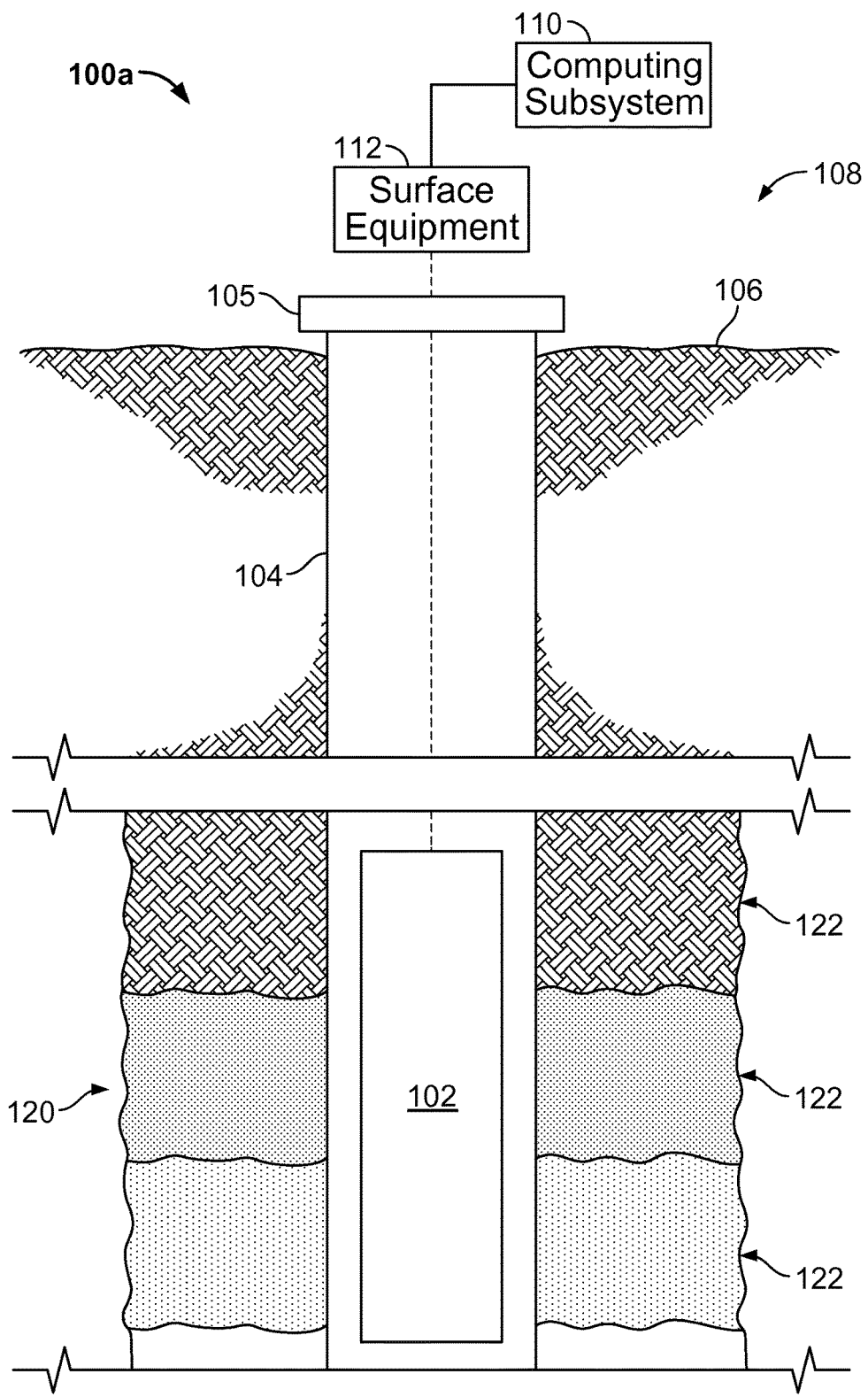
FIG. 1A is a diagram of an example well system.

FIG. 1A is a diagram of an example well system 100a. The example well system 100a includes an NMR logging system 108 and a subterranean region 120 beneath the ground surface 106. A well system can include additional or different features that are not shown in FIG. 1A. For example, the well system 100a may include additional drilling system components, wireline logging system components, etc.

The subterranean region 120 can include all or part of one or more subterranean formations or zones. The example subterranean region 120 shown in FIG. 1A includes multiple subsurface layers 122 and a wellbore 104 penetrated through the subsurface layers 122. The subsurface layers 122 can include sedimentary layers, rock layers, sand layers, or combinations of these and other types of subsurface layers. One or more of the subsurface layers can contain fluids, such as brine, oil, gas, etc. Although the example wellbore 104 shown in FIG. 1A is a vertical wellbore, the NMR logging system 108 can be implemented in other wellbore orientations. For example, the NMR logging system 108 may be adapted for horizontal wellbores, slant wellbores, curved wellbores, vertical wellbores, or combinations of these.

The example NMR logging system 108 includes a logging tool 102, surface equipment 112, and a computing subsystem 110. In the example shown in FIG. 1A, the logging tool 102 is a downhole logging tool that operates while disposed in the wellbore 104. The example surface equipment 112 shown in FIG. 1A operates at or above the surface 106, for example, near the well head 105, to control the logging tool 102 and possibly other downhole equipment or other components of the well system 100. The example computing subsystem 110 can receive and analyze logging data from the logging tool 102. An NMR logging system can include additional or different features, and the features of an NMR logging system can be arranged and operated as represented in FIG. 1A or in another manner.

In some instances, all or part of the computing subsystem 110 can be implemented as a component of, or can be integrated with one or more components of, the surface equipment 112, the logging tool 102 or both. In some cases, the computing subsystem 110 can be implemented as one or more computing structures separate from the surface equipment 112 and the logging tool 102.

In some implementations, the computing subsystem 110 is embedded in the logging tool 102, and the computing subsystem 110 and the logging tool 102 can operate concurrently while disposed in the wellbore 104. For example, although the computing subsystem 110 is shown above the surface 106 in the example shown in FIG. 1A, all or part of the computing subsystem 110 may reside below the surface 106, for example, at or near the location of the logging tool 102.

The well system 100a can include communication or telemetry equipment that allows communication among the computing subsystem 110, the logging tool 102, and other components of the NMR logging system 108. For example, the components of the NMR logging system 108 can each include one or more transceivers or similar apparatus for wired or wireless data communication among the various components. For example, the NMR logging system 108 can include systems and apparatus for wireline telemetry, wired pipe telemetry, mud pulse telemetry, acoustic telemetry, electromagnetic telemetry, or a combination of these and other types of telemetry. In some cases, the logging tool 102 receives commands, status signals, or other types of information from the computing subsystem 110 or another source. In some cases, the computing subsystem 110 receives logging data, status signals, or other types of information from the logging tool 102 or another source.

NMR logging operations can be performed in connection with various types of downhole operations at various stages in the lifetime of a well system. Structural attributes and components of the surface equipment 112 and logging tool 102 can be adapted for various types of NMR logging operations. For example, NMR logging may be performed during drilling operations, during wireline logging operations, or in other contexts. As such, the surface equipment 112 and the logging tool 102 may include, or may operate in connection with drilling equipment, wireline logging equipment, or other equipment for other types of operations.

Figure 1B:
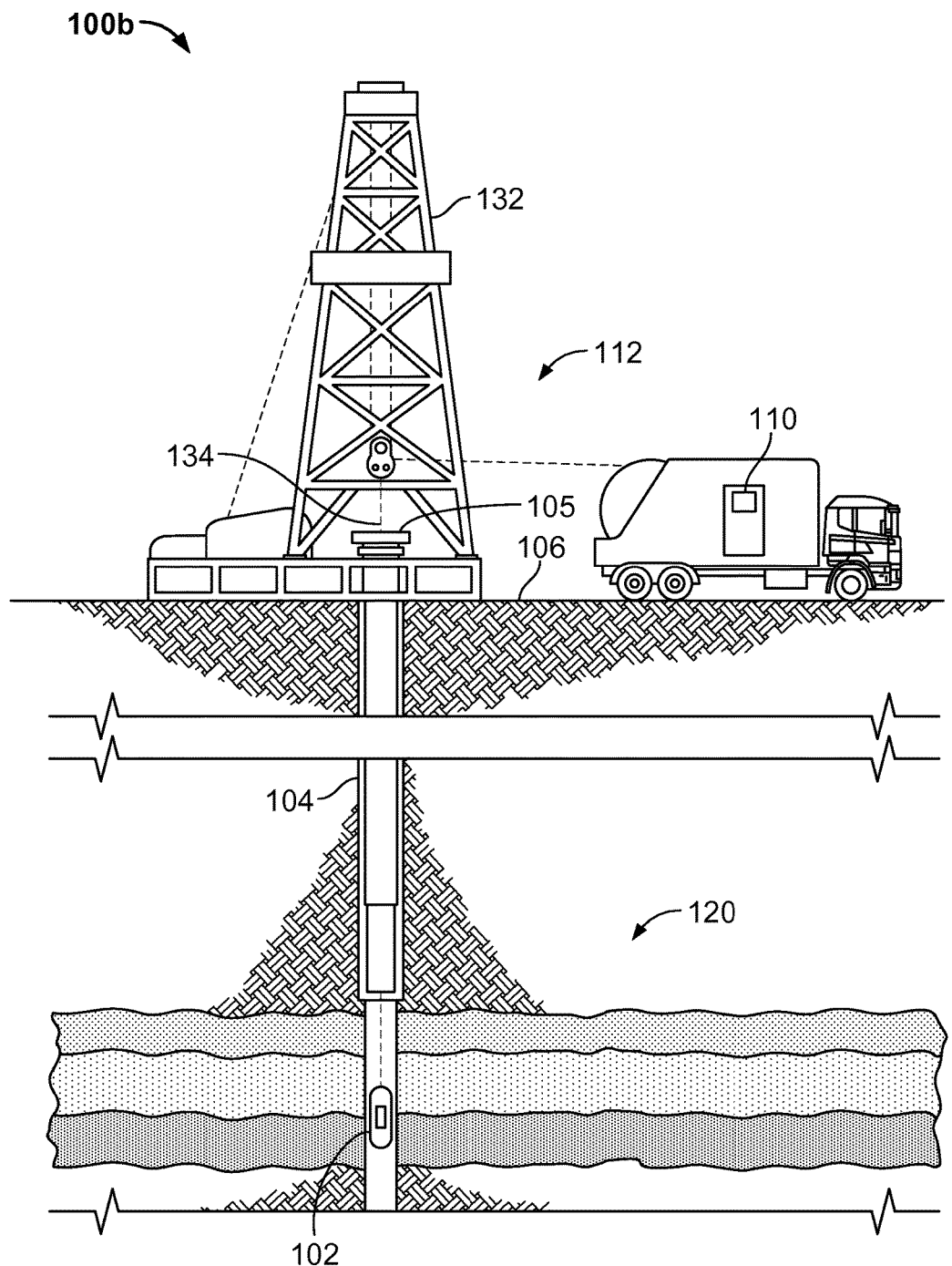
FIG. 1B is a diagram of an example well system that includes an NMR logging tool in a wireline logging environment.

In some examples, NMR logging operations are performed during wireline logging operations. FIG. 1B shows an example well system 100b that includes the NMR logging tool 102 in a wireline logging environment. In some example wireline logging operations, the surface equipment 112 includes a platform above the surface 106 equipped with a derrick 132 that supports a wireline cable 134 that extends into the wellbore 104. Wireline logging operations can be performed, for example, after a drill string is removed from the wellbore 104, to allow the wireline logging tool 102 to be lowered by wireline or logging cable into the wellbore 104.

Figure 1C:
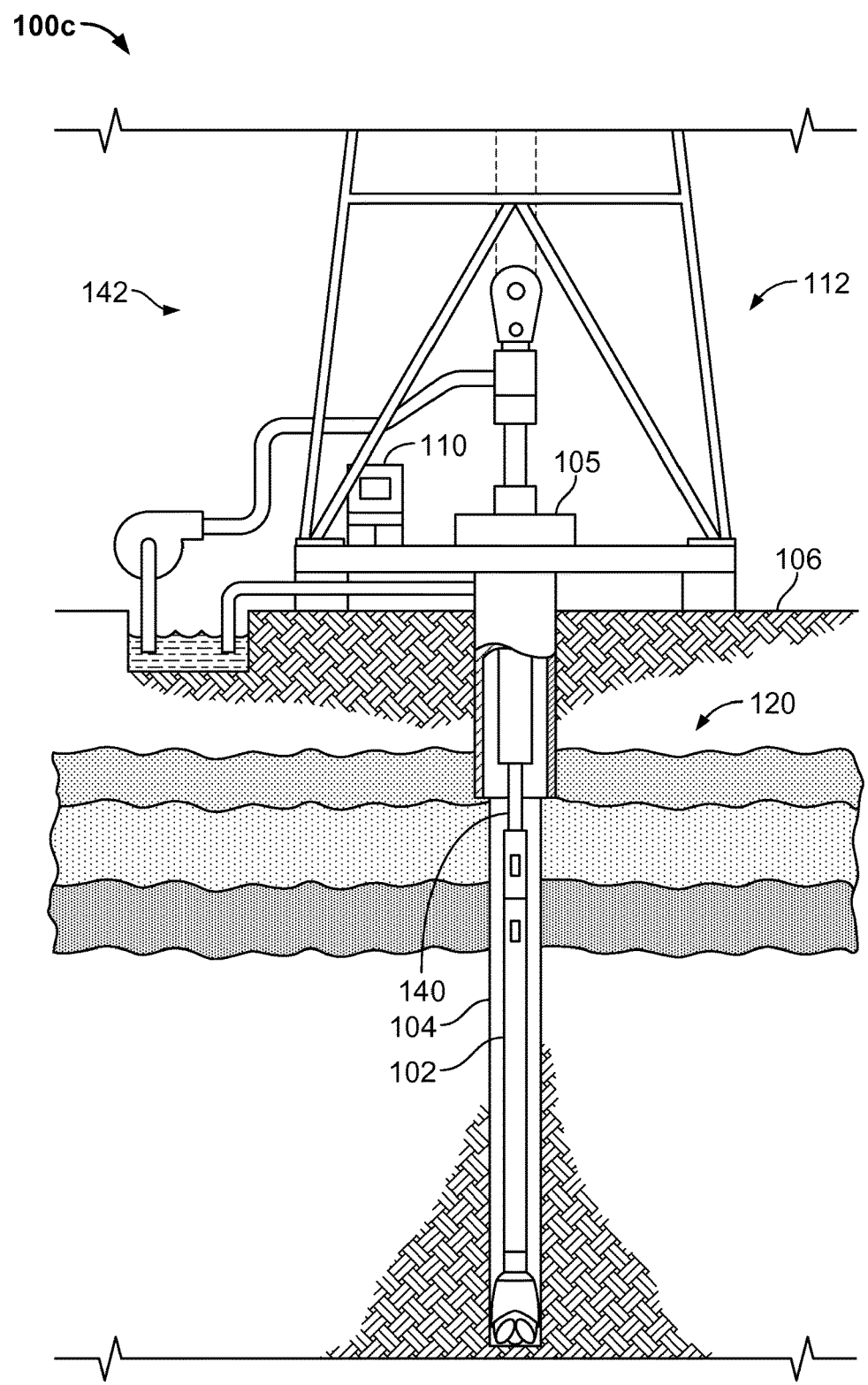
FIG. 1C is a diagram of an example well system that includes an NMR logging tool in a logging while drilling (LWD) environment.

In some examples, NMR logging operations are performed during drilling operations. FIG. 1C shows an example well system 100c that includes the NMR logging tool 102 in a logging while drilling (LWD) environment. Drilling is commonly carried out using a string of drill pipes connected together to form a drill string 140 that is lowered through a rotary table into the wellbore 104. In some cases, a drilling rig 142 at the surface 106 supports the drill string 140, as the drill string 140 is operated to drill a wellbore penetrating the subterranean region 120. The drill string 140 may include, for example, a kelly, drill pipe, a bottom hole assembly, and other components. The bottom hole assembly on the drill string may include drill collars, drill bits, the logging tool 102, and other components. The logging tools may include measuring while drilling (MWD) tools, LWD tools, and others.

In some example implementations, the logging tool 102 includes an NMR tool for obtaining NMR measurements from the subterranean region 120. As shown, for example, in FIG. 1B, the logging tool 102 can be suspended in the wellbore 104 by a coiled tubing, wireline cable, or another structure that connects the tool to a surface control unit or other components of the surface equipment 112. In some example implementations, the logging tool 102 is lowered to the bottom of a region of interest and subsequently pulled upward (e.g., at a substantially constant speed) through the region of interest. As shown, for example, in FIG. 1C, the logging tool 102 can be deployed in the wellbore 104 on jointed drill pipe, hard wired drill pipe, or other deployment hardware. In some example implementations, the logging tool 102 collects data during drilling operations as it moves downward through the region of interest. In some example implementations, the logging tool 102 collects data while the drill string 140 is moving, for example, while it is being tripped in or tripped out of the wellbore 104.

In some implementations, the logging tool 102 collects data at discrete logging points in the wellbore 104. For example, the logging tool 102 can move upward or downward incrementally to each logging point at a series of depths in the wellbore 104. At each logging point, instruments in the logging tool 102 perform measurements on the subterranean region 120. The measurement data can be communicated to the computing subsystem 110 for storage, processing, and analysis. Such data may be gathered and analyzed during drilling operations (e.g., during logging while drilling (LWD) operations), during wireline logging operations, or during other types of activities.

The computing subsystem 110 can receive and analyze the measurement data from the logging tool 102 to detect properties of various subsurface layers 122. For example, the computing subsystem 110 can identify the density, material content, or other properties of the subsurface layers 122 based on the NMR measurements acquired by the logging tool 102 in the wellbore 104.

In some implementations, the logging tool 102 obtains NMR signals by polarizing nuclear spins in the formation 120 and pulsing the nuclei with a radio frequency (RF) magnetic field. Various pulse sequences (i.e., series of radio frequency pulses, delays, and other operations) can be used to obtain NMR signals, including the Carr Purcell Meiboom Gill (CPMG) sequence (in which the spins are first tipped using a tipping pulse followed by a series of refocusing pulses), the Optimized Refocusing Pulse Sequence (ORPS) in which the refocusing pulses are less than 180°, a saturation recovery pulse sequence, and other pulse sequences.

The acquired spin-echo signals (or other NMR data) may be processed (e.g., inverted, transformed, etc.) to a relaxation-time distribution (e.g., a distribution of transverse relaxation times $T_2$ or a distribution of longitudinal relaxation times $T_1$, or both). The relaxation-time distribution can be used to determine various physical properties of the formation by solving one or more inverse problems. In some cases, relaxation-time distributions are acquired for multiple logging points and used to train a model of the subterranean region. In some cases, relaxation-time distributions are acquired for multiple logging points and used to predict properties of the subterranean region.

Figure 2:
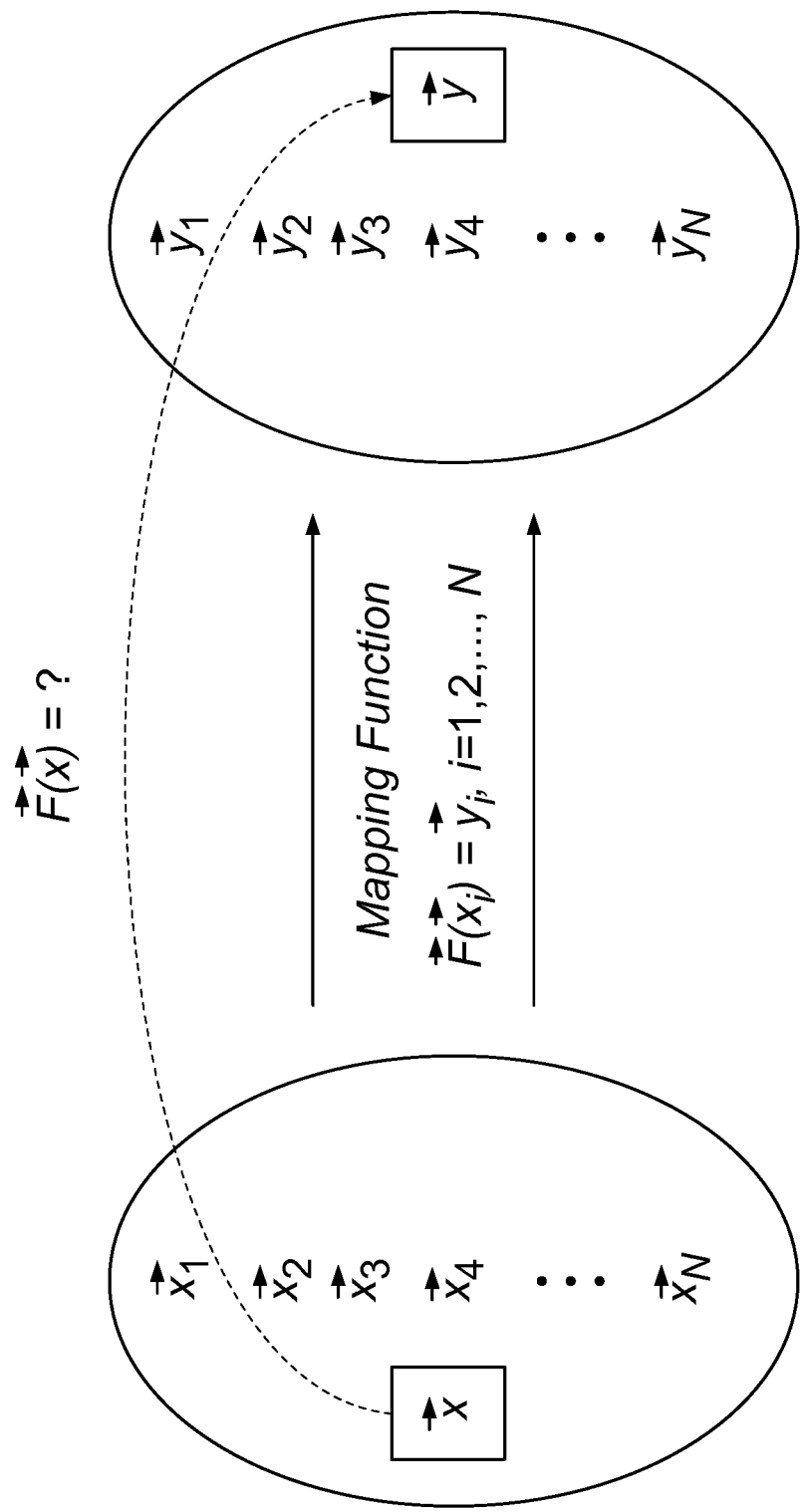
FIG. 2 is a diagram of an example mapping function.

Inverse problems encountered in well logging and geophysical applications may involve predicting the physical properties of some underlying system given a set of measurements (e.g., a set of relaxation-time distributions). Referring to FIG. 2, consider a database having a set of distinct input data $\vec{x}_i \in R^n$ (i.e., the inputs are n-dimensional vectors) and a set of corresponding outputs $\vec{y}_i \in R^m$, for i=1, ..., N, where N is the number of cases in the database. The different cases in the database represent different states of the underlying physical system. In this notation, $\vec{y}_i$ values represent samples of the function that one wants to approximate (e.g., by a model), and $\vec{x}_i$ values are the distinct points at which the function is given. The database is used to construct a mapping function such that, given measurements $\vec{x}$ that are not in the database, one can predict the properties $F(\vec{x})$ of the physical system that is consistent with the measurements. The mapping function can solve the inverse problem of predicting the physical properties of the system from the measurements.

Mapping functions can be used to solve the inverse problem of predicting the viscosity of fluid (e.g., oil, etc.) in a subterranean formation based on measurements obtained using NMR. In some cases, mapping can be used to develop a correlation that links fluid viscosity measurements with NMR measurements. A mapping function can be developed, for example, based on training data obtained through in situ measurements or ex situ measurements. The developed mapping function can then be used to predict the viscosity of oil based on subsequent in situ measurements. In some cases, Radial Basis Functions (RBFs) can be used to construct a subterranean formation viscosity model, and Principal Component Analysis (PCA) can be used to preprocess the data in the training database.

Figure 3:
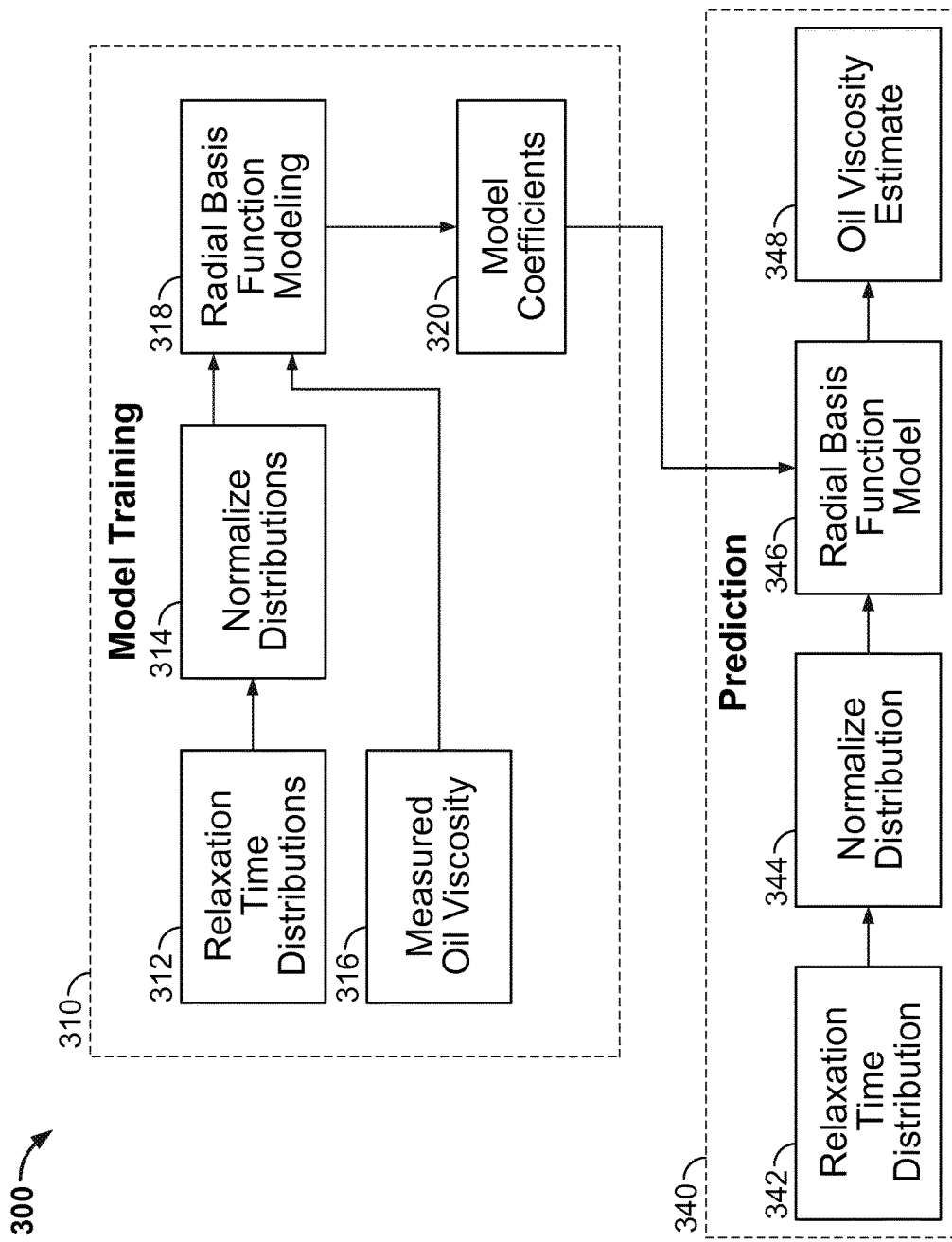
FIG. 3 is a diagram of an example process for modeling the viscosity of a subterranean formation.

An example process 300 for modeling the viscosity of fluid in a subterranean formation from NMR measurements is shown in FIG. 3. The example process 300 shown in FIG. 3 includes a model training sub-process 310 and a viscosity prediction sub-process 340. The model training sub-process 310 can be used to develop a mapping function based on a database of NMR and viscosity measurements; the viscosity prediction sub-process 340 can be used to predict viscosity based on one or more NMR measurements and the developed mapping function. The process 300 can include additional or different sub-processes or other operations, and the operations can be configured as shown or in another manner.

The example model training sub-process 310 includes generating a training database of relaxation distributions obtained from NMR measurements of fluids associated with one or more subterranean formations (312). Each distribution can be normalized to a common normalizing value (314). In some cases, each of the relaxation distributions can be reduced to a subset of key components (i.e., the "principal" components of the database) through principal component analysis. Measured viscosity values can be obtained by laboratory core plug viscosity measurements, measurements of fluids extracted from the subterranean region, measurement of fluids within the wellbore, or other types of measurements (316 of FIG. 3), or other techniques. The normalized distributions and the measured viscosity values can be used to train the RBF model (318). Training the RBF model generates model coefficients (320); the resulting RBF model and its coefficients can be used as a mapping function that predicts the viscosity of fluid in a subterranean formation based on input relaxation-time distributions.

In some implementations, the viscosity prediction sub-process 340 includes obtaining an input relaxation-time distribution from NMR logging of a subterranean formation (342), and normalizing the distribution to the same normalizing value that was used to normalize the training dataset (344). In some cases, the distribution is also converted to the same subset of principal components identified during model training. The processed relaxation-time distribution can then be used as an input in the RBF model, using the modeling coefficients identified during model training (346), resulting in a viscosity estimate (348).

In some examples, NMR signals are obtained in situ (e.g., by using NMR logging tools to obtain measurements of formations under the earth's surface). In some implementations, NMR signals can be obtained ex situ (e.g., by using NMR tools to obtain measurements of reservoir fluid samples and/or core plug samples that have been removed from the earth's surface). The NMR signals (obtained in situ or ex situ) can be converted into relaxation-time distributions. In some implementations, each NMR signal is a spin-echo train that includes a series of multi-exponential decays, and the relaxation-time distribution can be a histogram of the decay rates extracted from the spin-echo train.

In some cases, an NMR tool, for instance the logging tool 102, acquires multiple echo-time (TE) data of heavy oil samples. That is, multiple NMR signals are acquired in order to produce multiple relaxation-time distributions, each corresponding to a particular TE. Various pulse sequences (i.e., series of radio frequency pulses) can be used to obtain NMR signals, including the Carr Purcell Meiboom Gill (CPMG) sequence (in which the spins are first tipped using a tipping pulse followed by a series of refocusing pulses), the Optimized Refocusing Pulse Sequence (ORPS) in which the refocusing pulses are less than 180°, and other pulse sequences.

In some implementations (e.g., where diffusivity is not measured), gradient fields are not necessary, and a magnetic field gradient capability is not required for the NMR tool. In some instances, the NMR measurements can be carried out in a non-uniform static magnetic field. In some implementations NMR measurements are obtained by NMR tools that use magnetic field gradients and uniform static magnetic fields. In a gradient field, the measured $T_{2,m}$ can be expressed as $$\frac{1}{T_{2,m}} = \frac{1}{T_{2,intrinsic}} + \frac{\gamma^2 G^2 TE^2 D}{12}$$

For example, because the intrinsic relaxation time, $T_{2,intrinsic}$, of heavily oil can be fast and the diffusivity, D, of heavy oil can be low, the presence of magnetic field gradient, G, of strengths typically seen in NMR tools may not materially change the measured $T_2$ of heavy oil. That is, in some circumstances, the second term on the right side of the above equation may be much smaller than the first term.

The NMR signals (obtained in situ or ex situ) can be converted into relaxation-time distributions. NMR signal inversion is dependent on the inter-echo spacing TE used to acquire the signal. The inter-echo spacing can be controlled by the NMR measurement system, for example, by controlling the duration of the pulses and the timing between pulses in the pulse sequence executed by the NMR measurement system.

In some examples, each NMR signal is a spin-echo train that includes a series of multi-exponential decays, and the relaxation-time distribution can be a histogram of the decay rates extracted from the spin-echo train. For example, in some implementations, the inter-echo spacing TE dictates the upper limit of the fast $T_2$ component that can be measured by a particular NMR system. For NMR signals acquired using a Carr Purcell Meiboom Gill (CPMG) pulse sequence, the decay of NMR signals can be described by a multi-exponential decay function. For example, an NMR signal can be described as multiple components resulting from multiple difference relaxation times in the measured region. For example, the signal amplitude of the first echo may be expressed approximately by:

$$\phi(t = TE) = \sum_{i=1}^{N} \phi_i \exp\left(-\frac{TE}{T_{2i}}\right).$$

Here, each of the components has a respective amplitude of $\phi_i$ and a characteristic relaxation time $T_{2i}$.

In some cases, some of the components ($i<k$) (those having the shortest relaxation times $T_{2i}$) decay too quickly to produce a measureable signal at the echo time, and the measurable signal amplitude is:

$$\sum_{i=k}^{N} \phi_i,$$

and the total signal is:

$$\sum_{i=1}^{N} \phi_i.$$

Accordingly, the apparent hydrogen index ($HI_{app}$) can be expressed as:

$$HI_{app}(TE) = \frac{\sum_{i=k(TE)}^{N} \phi_i}{\sum_{i=1}^{n} \phi_i}.$$

The $T_2$ distribution can then be described as:

$\phi : \{\phi_i \text{ vs. } T_{2i}, \text{ where } i=1:N\}$.

For data acquired with a finite TE, the apparent $T_2$ distribution can be described as:

$\phi_{app}(TE):\{\phi_i \text{ vs. } T_{2i}, \text{ where } i=k:N \text{ and } \phi_i=0 \text{ for } i<k\}$.

Figure 4:
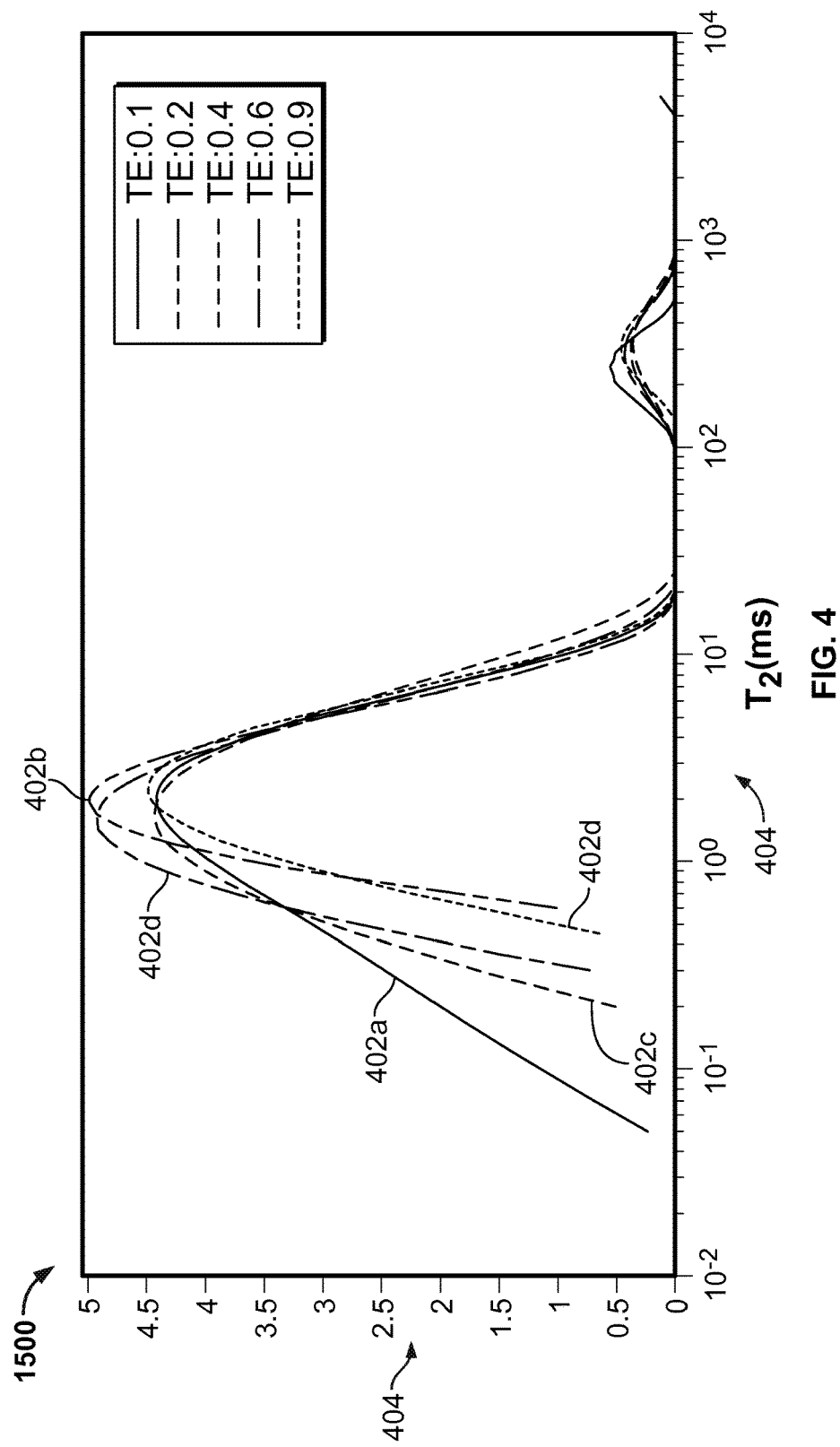
FIG. 4 includes plots of example $T_2$ distributions for each of several spin-echo times (TEs).

Multiple TEs can be used to acquired NMR data, and can result in multiple apparent $T_2$ distributions, each corresponding to a particular TE. Example $T_2$ distributions 402a-e for each of several TEs is shown in FIG. 4, where the horizontal axis 404 represents the range of $T_2$ times and the vertical axis 404 represents the relative frequency of occurrence of each $T_2$ time.

Other NMR inversion techniques can be used to obtain other relaxation-time distributions. The relaxation-time distributions can include distributions of transverse relaxation times or longitudinal relaxation times obtained from NMR data. In some cases, the sum of the amplitudes of each distribution is normalized to a common normalizing value. For example, the normalizing value can be 1 or another constant value. To normalize a distribution, the values in the distribution can be multiplied or scaled uniformly so that the amplitudes in the normalized distribution sum to the normalizing value.

The relaxation-time distributions of the training database can be normalized to the common normalizing value. This may be beneficial in some circumstances, as viscosity may depend primarily on the shape of the $T_2$ distribution rather than on the amplitude of the distribution. By normalizing the $T_2$ distribution, the RBF model can be developed such that it considers the shape of the shape of the $T_2$ distribution rather than on the amplitude of the distribution. The relaxation-time distribution can be normalized according to various common normalizing values. For instance, in some implementations, the relaxation-time distributions can be normalized to a common normalizing value of one (i.e., normalized such that each relaxation-time distribution has a unit integral). In some implementations, the relaxation-time distribution can be normalized to other common normalizing values (e.g., 0.5, 1.5, 2, 2.5, and so forth).

Viscosity values can be obtained using different means other than NMR for the subterranean formations (316 of FIG. 3). For the purposes of model training, these measured viscosity values can be obtained independently and treated as "ground truth" values, and can be used to determine correlations between the measured NMR signals and corresponding viscosity values. In some implementations, these viscosity values are obtained ex situ using any of a variety of viscosity measurement instruments and techniques. For example, in some implementations, a core sample from the formation is removed from the earth's surface, and fluid from the core sample is measured using a viscometer or another type of system. In another example, a reservoir fluid sample is removed from the earth's surface, and the reservoir fluid sample is measured using a viscometer or another type of system.

The training database and the measured viscosity values can be used to train an RBF model. A radial basis function (RBF) is a function in the form of $\varphi(\|\vec{x}-\vec{x}_c\|)$, where $\|\vec{x}-\vec{x}_c\|$ is the Euclidean distance between the points $\vec{x}$ and $\vec{x}_c$, and where $\vec{x}$ is the variable and $\vec{x}_c$ is the center of the radial basis function. An RBF model $F(\vec{x})$ can be represented as a linear combination of radial basis functions. The RBF model can be used to approximate the physical system $f(\vec{x})$ to a certain degree of accuracy, for example, assuming the underlying physical system $f(\vec{x})$ is smooth and continuous.

The RBF model $F(\vec{x})$ is derived by interpolating an input-output data set $\{(\vec{x}_i,\vec{y}_i)\}_{i=1}^{N}$ sampled from an underlying physical system $f(\vec{x})$, where $\{\vec{x}_i\}_{i=1}^{N}$ is the input data set, and $\{\vec{y}_i\}_{i=1}^{N}$ is the output data set. The input data set can include, for example, the database of relaxation-time distributions, the corresponding TEs and other information for each of the distributions. The output data set can include the measured viscosity corresponding to each relaxation-time distribution. An RBF model can be represented $$F(\vec{x}_i) = \vec{y}_i, i = 1, 2, ..., N,$$

where, $$F(\vec{x}) = \sum_{i=1}^{N} \vec{w}_i \varphi(\|\vec{x}-\vec{c}_i\|).$$

In this example model, $\{\vec{w}_i \varphi(\|\vec{x}-\vec{c}_i\|)\}_{i=1}^{N}$ is a set of weighted RBFs, N, $\vec{w}_i$, and $\vec{c}_i$ are model coefficients, and $\{(\vec{x}_i,\vec{y}_i)\}_{i=1}^{N}$ is the input-output training set.

In the above model, the parameters:

$\{(\vec{c}_i)\}_{i=1}^{N}$ represent the centers of the RBF model. In some implementations, the centers correspond to the inputted training parameters which may include, for example, the database of relaxation-time distributions, principle components of the normalized relaxation-time distributions, the corresponding TEs for each of the distributions, the measured viscosities, or combinations of these and other input training parameters. In this case, the RBF model can be represented as:

$$F(\vec{x}) = \sum_{i=1}^{N} \vec{w}_i \varphi(\|\vec{x} - \vec{x}_i\|),$$

where N, $\vec{w}_i$, and $\vec{x}_i$ are the model coefficients. The function $\varphi$ can be a Gaussian function or another type of smooth function. For example, when the function $\varphi$ is a Gaussian, the matrix associated with the interpolation is well-conditioned, and the RBF inversion has a unique solution.

The coefficients of the RBF model can be determined by interpolation of the training datasets. In some instances, the coefficients $\vec{w}_i$ can be determined by requiring that the interpolation equations be satisfied exactly. For example, the coefficients can be a linear combination of the function values $$\vec{w}_i = \sum_{j=1}^{N} \Phi_{ij}^{-1} \vec{y}_j,$$

where $\phi_{ij} = \varphi(\|\vec{x}_i - \vec{x}_j\|)$ is the N×N interpolation matrix.

The RBF model and model coefficients can be used to predict viscosity based on an input relaxation-time distribution. An input relaxation-time distribution can be obtained from an input NMR signal, for example, using NMR signal inversion. Typically, this input NMR signal is obtained independently from the NMR signals used to train the model. For example, the input NMR signal can be obtained from a subterranean formation that contains oil or other fluids having unknown viscosity. The input NMR signal is inverted to produce a relaxation-time distribution using an NMR inversion process similar to the NMR signal inversion described above.

The input relaxation-time distribution can then be normalized to the same common normalizing value used in model training. In some cases, the input relaxation-time distribution can then be remapped to a new coordinate system identified during principal component analysis of the model training. The processed relaxation-time distribution data and corresponding TE value can be provided as inputs to the RBF model, using the model coefficients identified during model training (346 of FIG. 3). For example, if $\vec{x}$ is the input relaxation-time distribution and the corresponding TE value, the estimated viscosity $F(\vec{x})$ can be determined by:

$$F(\vec{x}) = \sum_{i=1}^{N} \vec{w}_i \varphi(\|\vec{x} - \vec{c}_i\|),$$

where N, $\vec{w}_i$, and $\vec{c}_i$ are the model coefficients identified during model training. Thus, after modeling training, subsequent viscosity estimates (348 of FIG. 3) can be determined using independently acquired input NMR signals.

Figure 5:
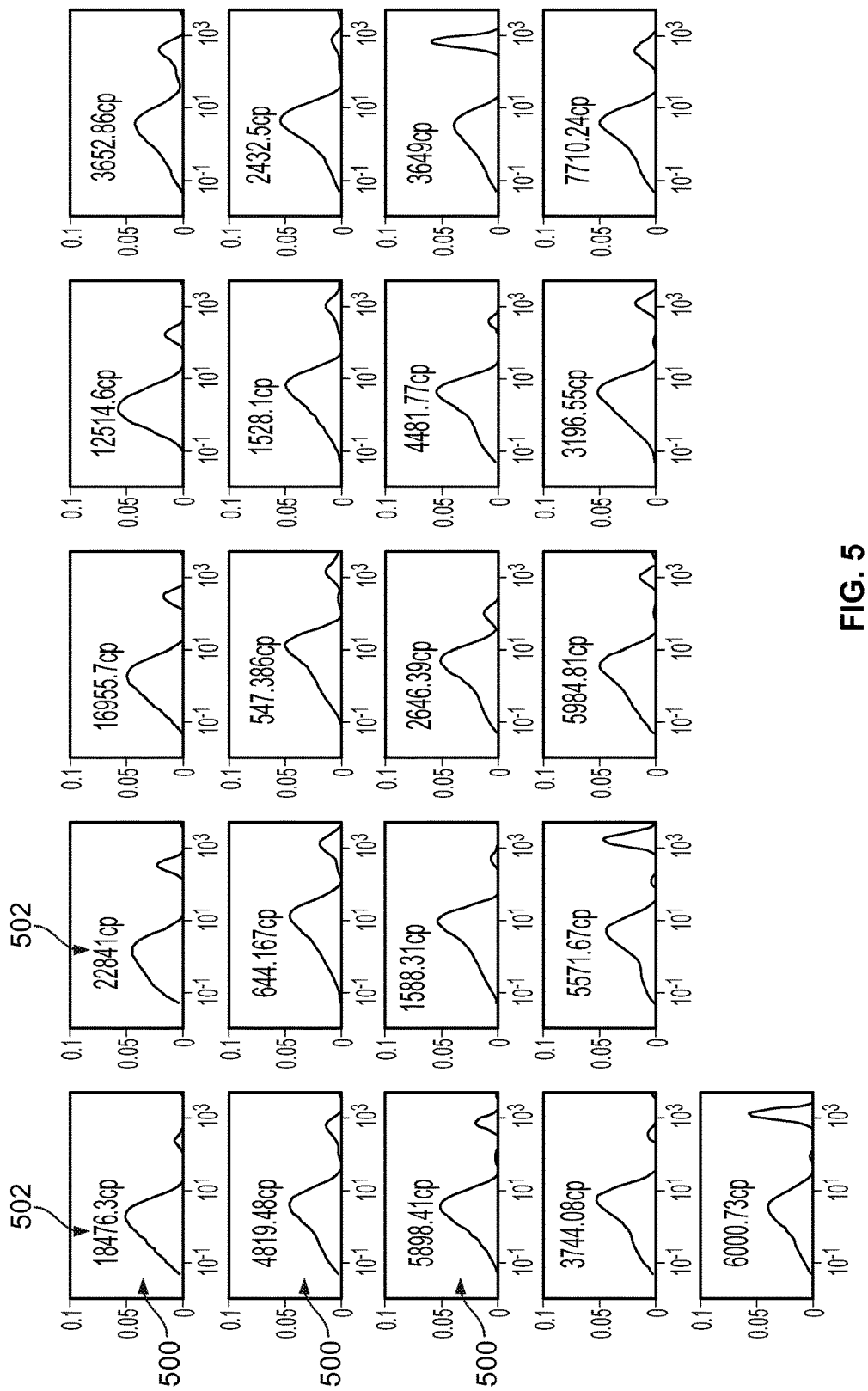
FIG. 5 includes plots of an example training database that includes 21 samples measured using one spin-echo time.

The performance of the RBF model can be determined by comparing the viscosity predicted by the RBF model to the measured viscosity using a "leave one out" method, in which a sample from the training data set is taken out and its viscosity is predicted using the RBF model developed with the rest of the data in the training data set. Referring to FIG. 5, an example input database includes 21 samples, each measured using TEs of 0.1 ms, 0.4 ms, 0.6 ms, 0.9 ms, and 1.2 ms. FIG. 5 shows the resulting $T_2$ distribution 500 for each of the samples when measured using a TE of 0.1 ms, and the corresponding viscosity value 502 (as measured by a viscometer) is shown in the corner of each plot. Using the "leave one out method," each sample can be removed from the training database one at a time, and its viscosity can be predicted using an RBF model trained using the remaining samples. This process can be repeated for all the samples in the database.

Figure 6A:
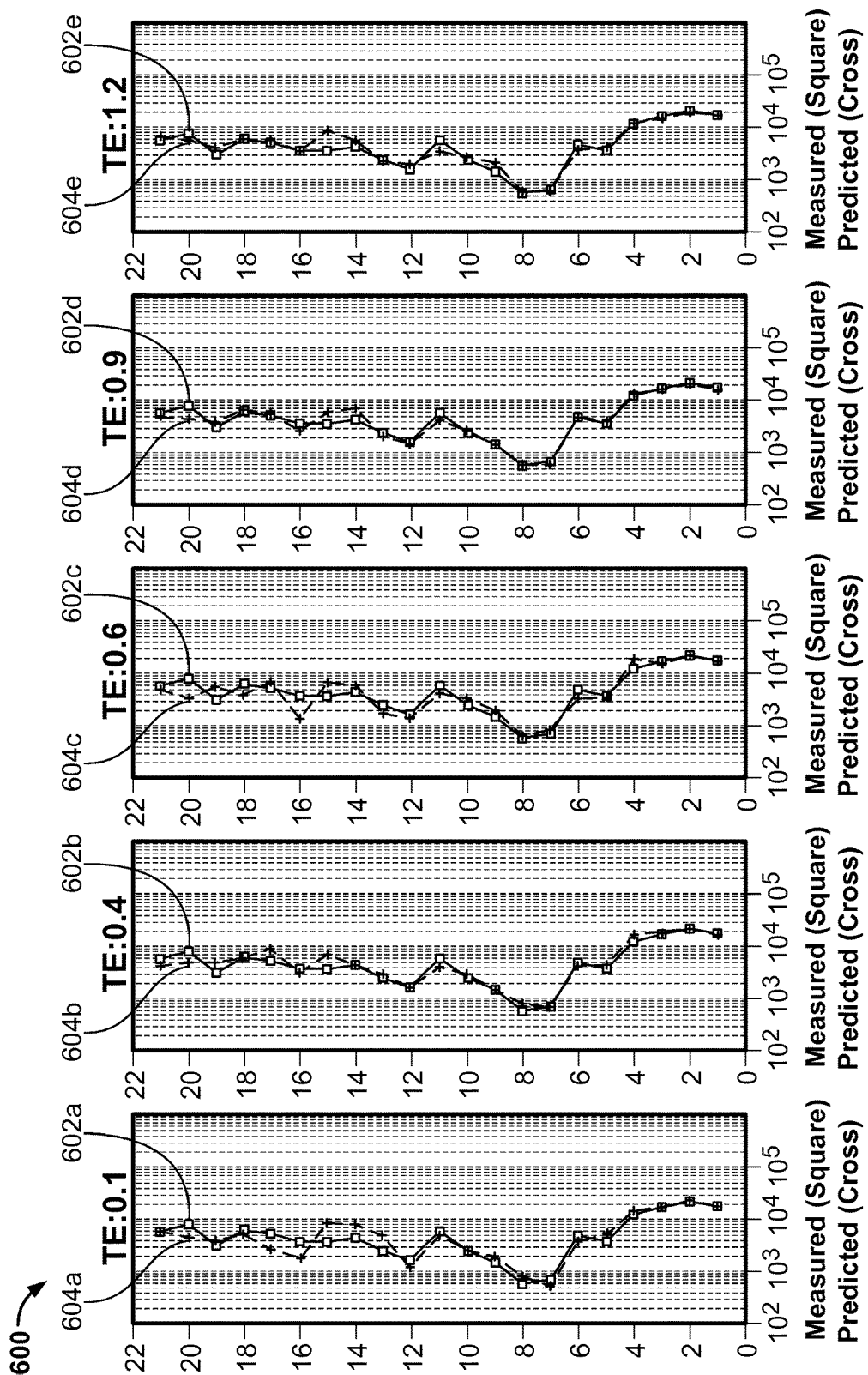
FIGS. 6A-B includes plots comparing the measured viscosities and predicted viscosities from an example radial basis function (RBF) model.
Figure 6B:
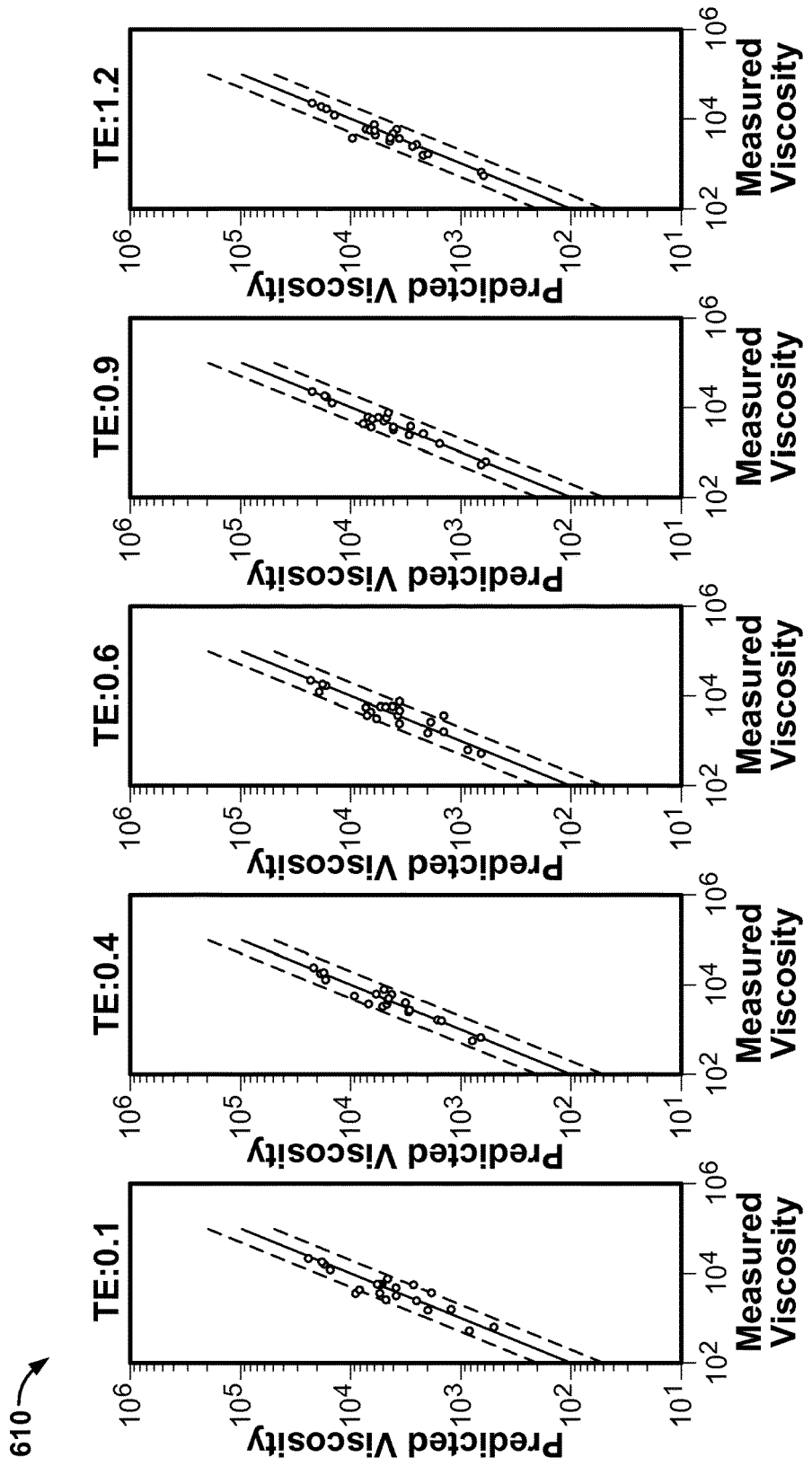

FIGS. 6A and 6B show the comparisons between the measured viscosities and predicted viscosities from the RBF model. For clarity, the results from each TE are plotted separately even though all the data were used together for the RBF model. As shown in FIG. 6A, plots 600 compare the measured viscosities 602a-e and the predicted viscosities 604a-e for each of the 21 samples. In FIG. 6B, plots 610 show this comparison as a scatter plot. Using this example training database, the viscosity predicted using the RBF model is generally well within one order of magnitude or less of the measured viscosity.

Figure 7A:
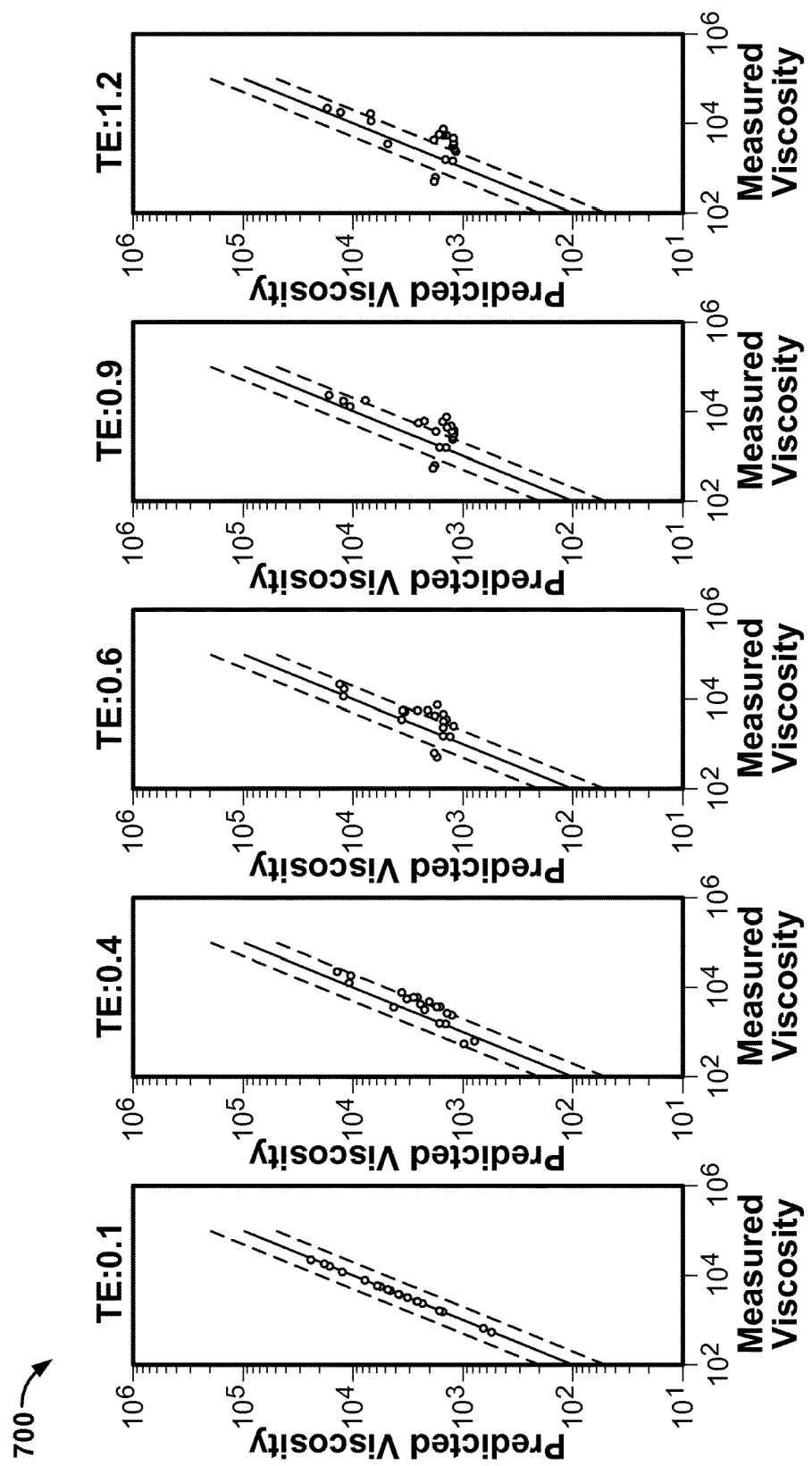
FIGS. 7A-B include plots showing the predictive performance of example RBF models trained using $T_2$ distributions acquired with the same TE, and used to predict viscosities based on $T_2$ distributions acquired with different TEs.
Figure 7B:
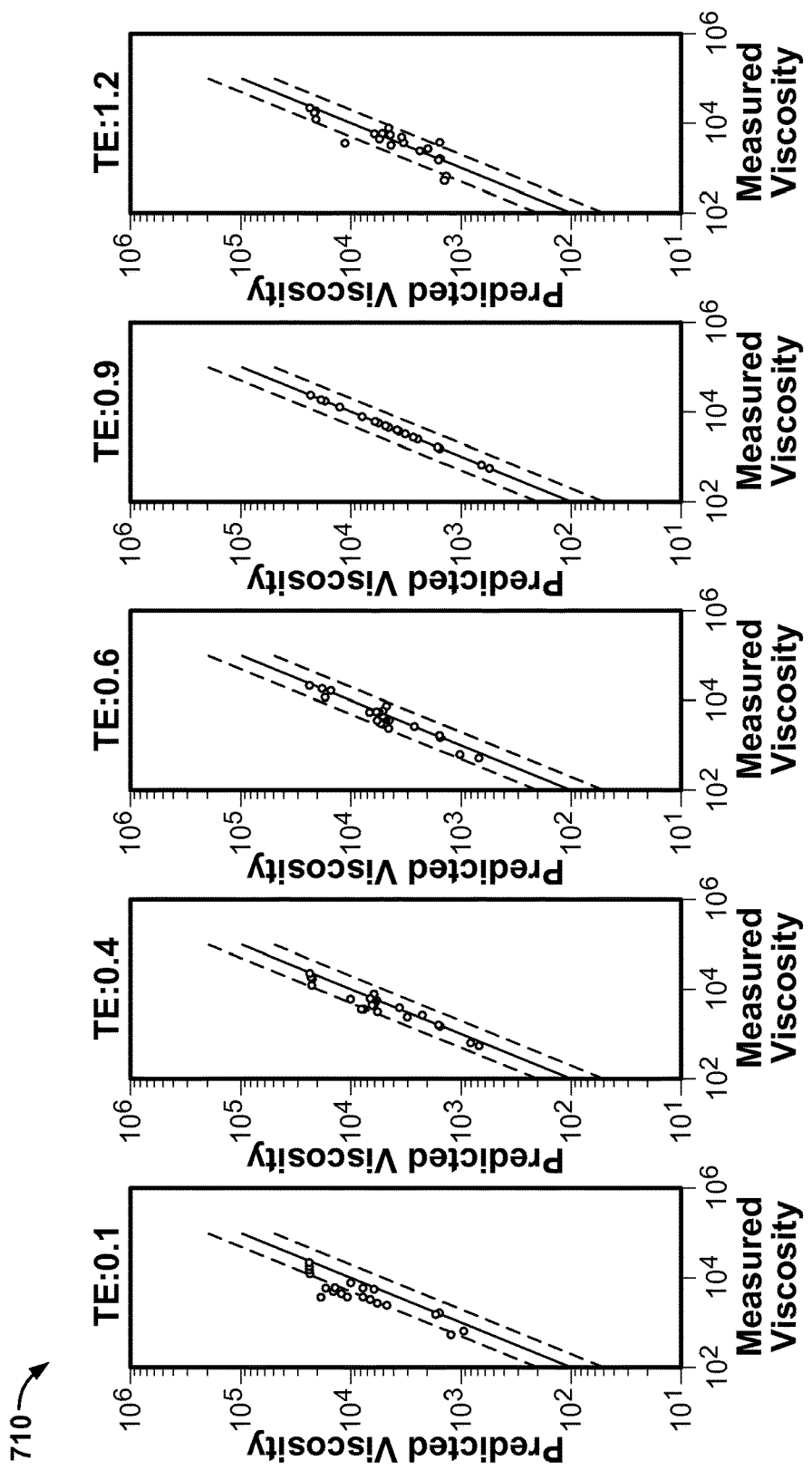

In some implementations, a model trained with data acquired using multiple TEs provides viscosity estimates that are more accurate than a model trained with data acquired using only a single TE. FIGS. 7A-B illustrate an example of an advantage of using training data acquired using a range of different TE acquisitions. In FIGS. 7A-B, an example RBF model is trained using $T_2$ distributions acquired with the same TE, and the model is used to predict viscosities based on $T_2$ distributions acquired with different TEs. Referring to FIG. 7A, the RBF model was trained using $T_2$ distributions acquired with a TE of 0.1 ms, then used to predict viscosities based on $T_2$ distributions acquired with TEs of 0.4 ms, 0.6 ms, 0.9 ms, and 1.2 ms. A comparison between the measured viscosity and the predicted viscosity is shown in plots 700. Referring to FIG. 7B, the RBF model was trained using $T_2$ distributions acquired with a TE of 0.9 ms, then used to predict viscosities based on $T_2$ distributions acquired with TEs of 0.1 ms, 0.4 ms, 0.6 ms, and 1.2 ms. A comparison between the measured viscosity and the predicted viscosity is shown in plots 710. FIGS. 7A-B illustrate that models trained using a single TE can more accurately predict viscosity values based on $T_2$ distributions acquired with the same TE, and the models provide less accurate predictions of viscosity values based on $T_2$ distributions acquired with different TEs.

In some implementations, training a model with training data from multiple TE values can improve the prediction accuracy of the model. The input data set used to train the model may additionally include each $T_2$ distribution's apparent hydrogen index value, $HI_{app}(TE_j)$. The apparent hydrogen index value $HI_{app}(TE_j)$ can be calculated as the integral of a $T_2$ distribution's amplitude, normalized by the apparent porosity determined from the shortest TE measurement. As discussed earlier, in some implementations, the $T_2$ distributions with larger inter-echo times (TEs) fail to detect very fast relaxation components. In such cases, $HI_{app}(TE_j)$ can be used as another input parameter to compensate these missing components. Further, because the missing fast $T_2$ components effectively distort the $T_2$ distribution shape, the normalized $T_2$ distribution patterns may already contain some information about the missing signal amplitude. Because the apparent hydrogen index can depend on this missing signal amplitude, the apparent hydrogen index can serve as an optional input parameter during model training.

Figure 8A:
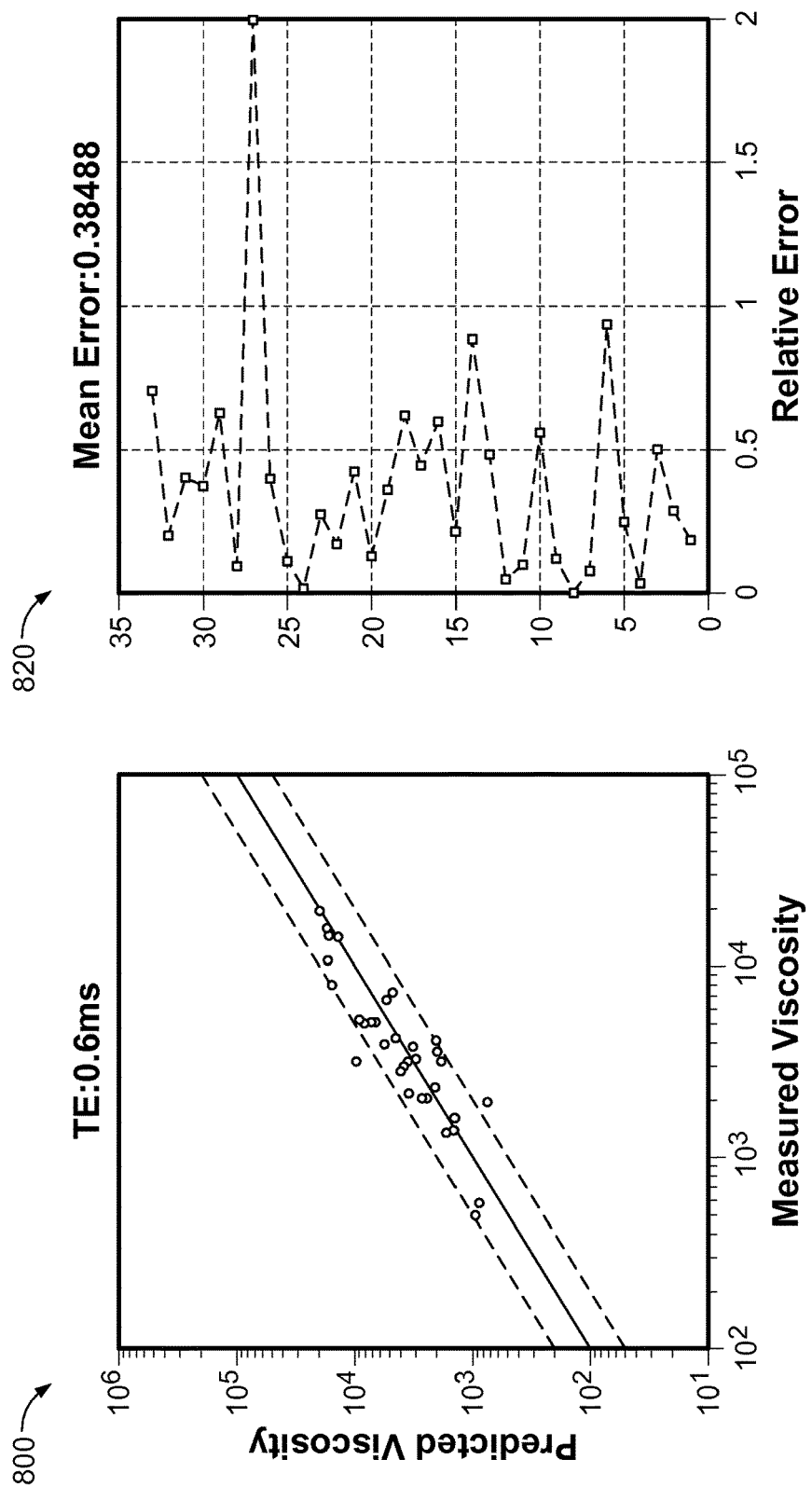
FIGS. 8A-B include plots comparing results of the example RBF model with and without the inclusion of the apparent hydrogen index during model training.
Figure 8B:
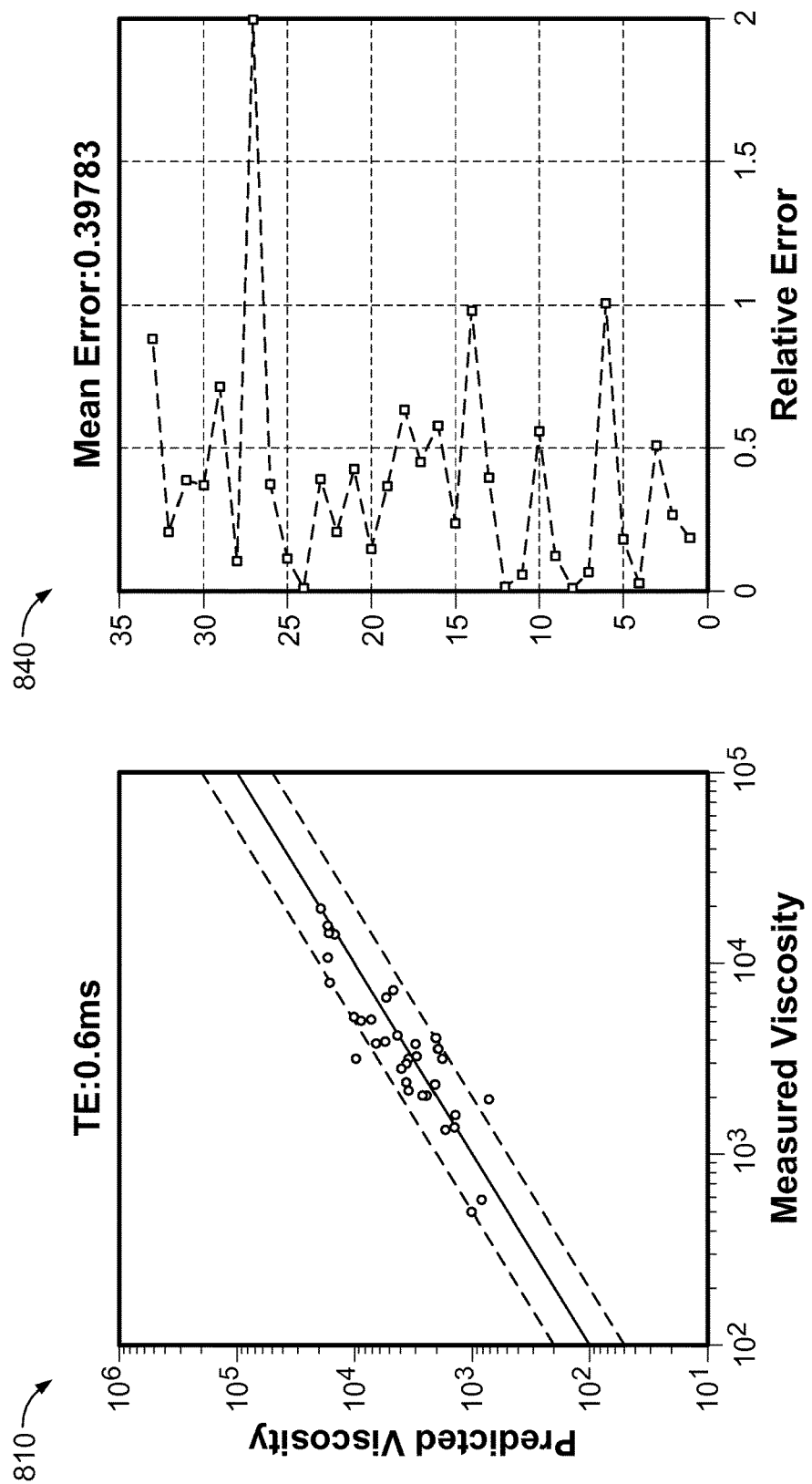

FIGS. 8A-B show a comparison of results of an example RBF model with (plot 800 of FIG. 8A) and without (810 of FIG. 8B) the inclusion of the apparent hydrogen index ($HI_{app}$) during model training. The example RBF models are trained with $T_2$ distributions derived from measurements acquired using TEs of 0.1 ms, 0.4 ms, 0.9 ms and 1.2 ms, and $T_2$ distributions derived from measurements acquired using a TE of 0.6 ms are used to predict the viscosities. As shown in FIGS. 8A-B, in terms of the relative error of the predictions as shown in plots 820 and 840, the performance of the RBF model training using $HI_{app}$ is better than the one trained without $HI_{app}$. In some implementations, the degree of benefit in training a model using $HI_{app}$ depends on the number of fast relaxation components in the sample.

A $T_2$ distribution is affected by noise in the measurement and the inversion process, and these uncertainties can affect the accuracy of the RBF model. To lessen the effects of noise, in some implementations, instead of using $T_2$ distributions directly during model training and prediction, the $T_2$ distribution can be divided into a number of segments, where $P_i(TE_j)$ is the partial porosity of the $i^{th}$ segment for a $T_2$ distribution derived from a measurement acquired using $TE_j$. The $T_2$ distribution can be divided based on various criteria. For example, in some implementations, the $T_2$ distribution is divided into segments based on previously acquired $T_2$ distributions of substances expected to be in a particular reservoir. Thus, the $T_2$ distributions can be segmented in a manner that accentuates differences between various substances expected to be within a particular reservoir. Accordingly, in some implementations, the input parameters of the RBF can be described as:

$$\{TE_j, [P_i(TE_j)]_{i=1}^{i=N}, HI_{app}(TE_j)\},$$

where N is the number of segments from the $T_2$ distribution. The correlation between the viscosity and input parameters can be described as:

$$\eta = R(TE, HI_{app}, P(TE)),$$

where R is the trained RBF model.

In some implementations, in order to mitigate the effects of over-fitting, the RBF model can be regularized according to a cost function that penalizes oscillatory behavior. The measurement data with noise can be described by:

$$F(\vec{x}_i) = \vec{y}_i + \varepsilon_i, i = 1, 2, \ldots, N,$$

where $$F(\vec{x}) = \sum_{i=1}^{N} \vec{w}_i \varphi(\|\vec{x} - \vec{x}_i\|),$$

assuming the centers of the RBF functions are the set of training inputs, and $\varepsilon_i$ is the noise in the measurement data. The RBF model can be obtained by minimizing the following cost function:

$$E(F) = \sum_{i=1}^{N} (F(\vec{x}_i) - \vec{y}_i)^2 + \lambda \sum_{i=1}^{N} \vec{w}_i^2,$$

where $$\sum_{i=1}^{N} (F(\vec{x}_i) - \vec{y}_i)^2$$

is the fitting error, and $$\sum_{i=1}^{N} \vec{w}_i^2$$

is the regularization term to penalize the oscillations in the fitting. The parameter $\lambda$ controls the balance between fitting the data and avoiding the penalty, and can be assigned different values depending on the desired fitting behavior. In some implementations, the value of parameter $\lambda$ can be determined using generalized cross-validation methods in order to assess the accuracy of the resulting RBF model. Example cross-validation methods include K-fold cross validation, repeated random sub-sampling validation, and leave-one-out cross-validation.

Figure 9A:
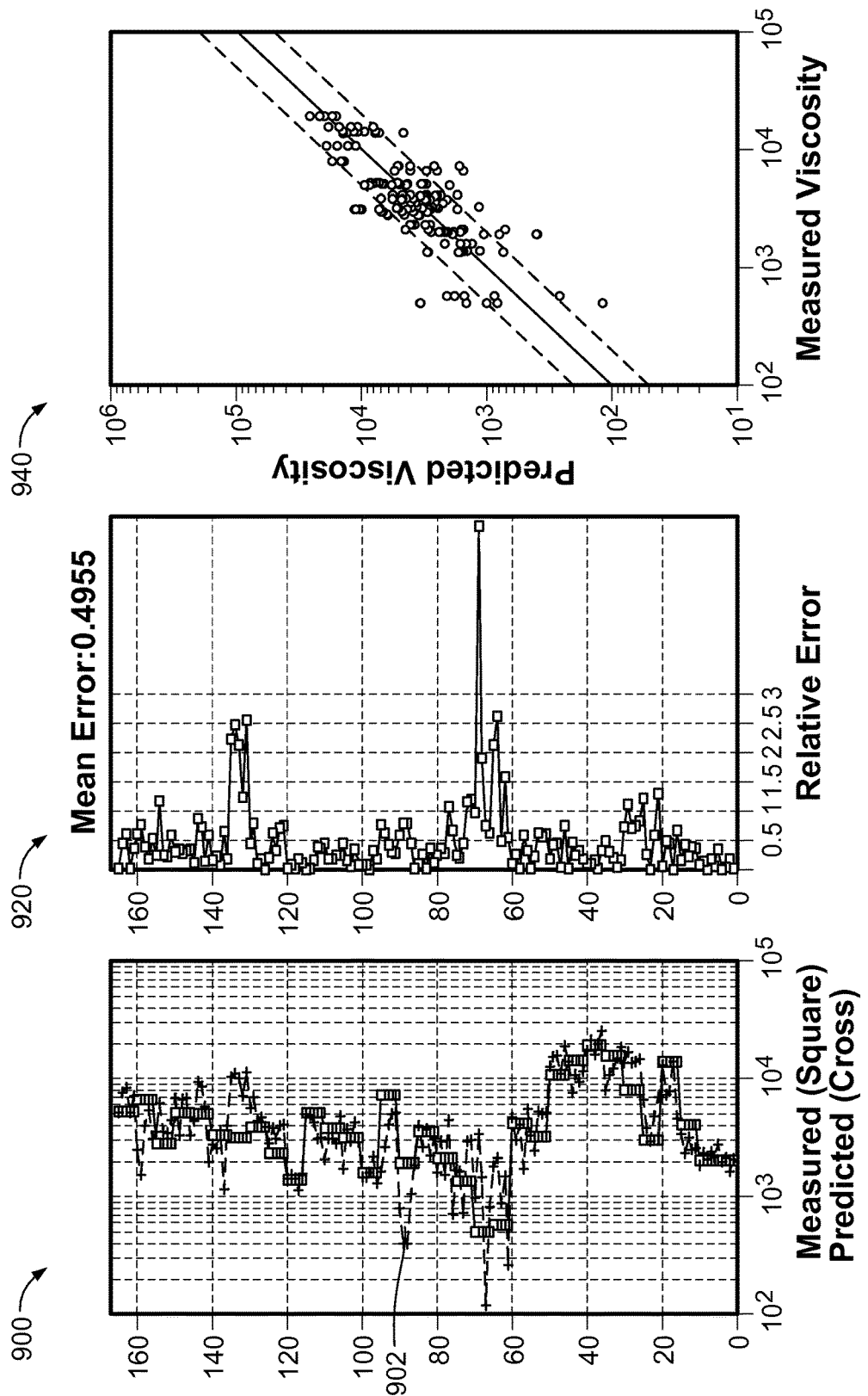
FIGS. 9A-B include plots comparing the viscosity predictions of the example RBF model and the viscosity predictions of the regularized RBF model.
Figure 9B:
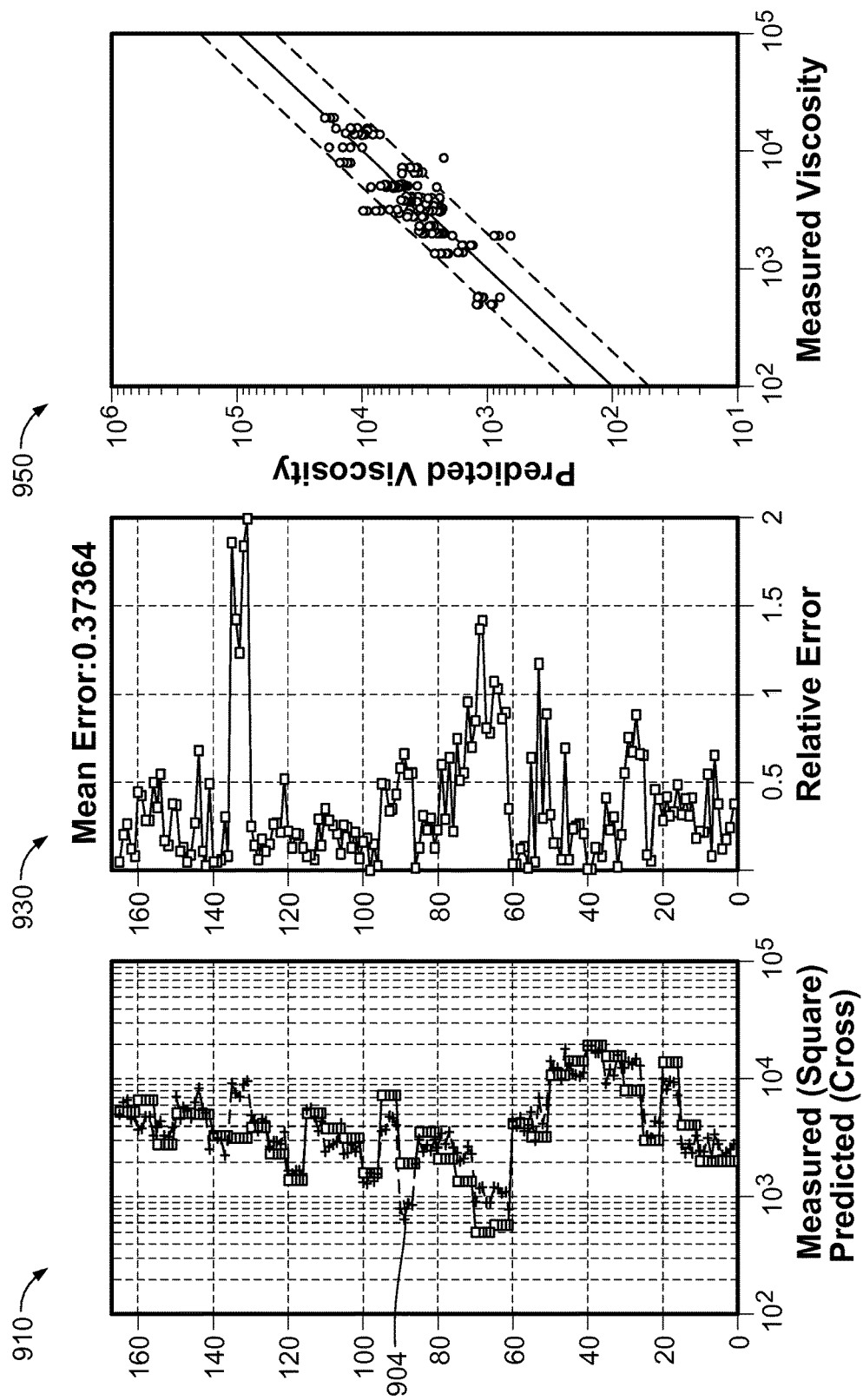

FIGS. 9A-B show a comparison between the viscosity predictions of the example RBF model, without regularization (FIG. 9A) and with regularization (FIG. 9B). The predictions based on the regularized RBF model exhibit a lesser degree of over-fitting compared to that of the non-regularized RBF model. For example, referring to plot 900 of FIG. 9A, the viscosities 902 predicted by the non-regularized RBF model exhibit a greater degree of oscillatory behavior compared to the viscosities 904 predicted by the regularized RBF model in plot 910 of FIG. 9B. Regularizing the RBF model can also increase the accuracy of the prediction by reducing the relative error of the predictions. For example, plots 920 and 930 of FIGS. 9A-B show the relative error of the predicted viscosities for the non-regularized RBF model and the regularized RBF model, respectively. Regularizing the RBF model can also reduce the overall spread of the predictions. For example, plots 940 and 950 of FIGS. 9A-B compare the predicted viscosities to the measured viscosities as a scatter plot.

In some implementations, the effects of noise can be lessened by using Principal Component Analysis (PCA) to reduce the training database of relaxation-time distributions to a subset of key components. In some cases, PCA provides a rank ordering of variances in the data. The rank ordering can be structured such that principal components with larger associated variances represent important structure (signal), while those with lower variances represent noise or less significant information.

In some implementations, Principal Component Analysis (PCA) transforms a set of data vectors from an initial coordinate system to a new coordinate system. The new coordinate system can be defined such that when the data vectors are expressed in the new coordinate system, all (or substantially all) significant variations among the data vectors are described by a reduced number of vector components. Thus, although the data vectors may have the same number of components in both coordinate systems, most of the vector components in the new coordinate system can be ignored or neglected; the retained vector components form a set of principal components that can be used to analyze the data.

In some cases, the $k^{th}$ principal component is the $k^{th}$ component of a transformed data vector in the new coordinate system. The proportion of the total variance accounted for by $k^{th}$ principal component can be:

$$\frac{\lambda_k}{\sum_{i=1}^{n} \lambda_i},$$

where $\lambda_i$, i=1, ..., n are the eigenvalues of the covariance matrix of the training data set. Here, each of the eigenvalues quantifies the variance of the corresponding principal component.

Figure 10:
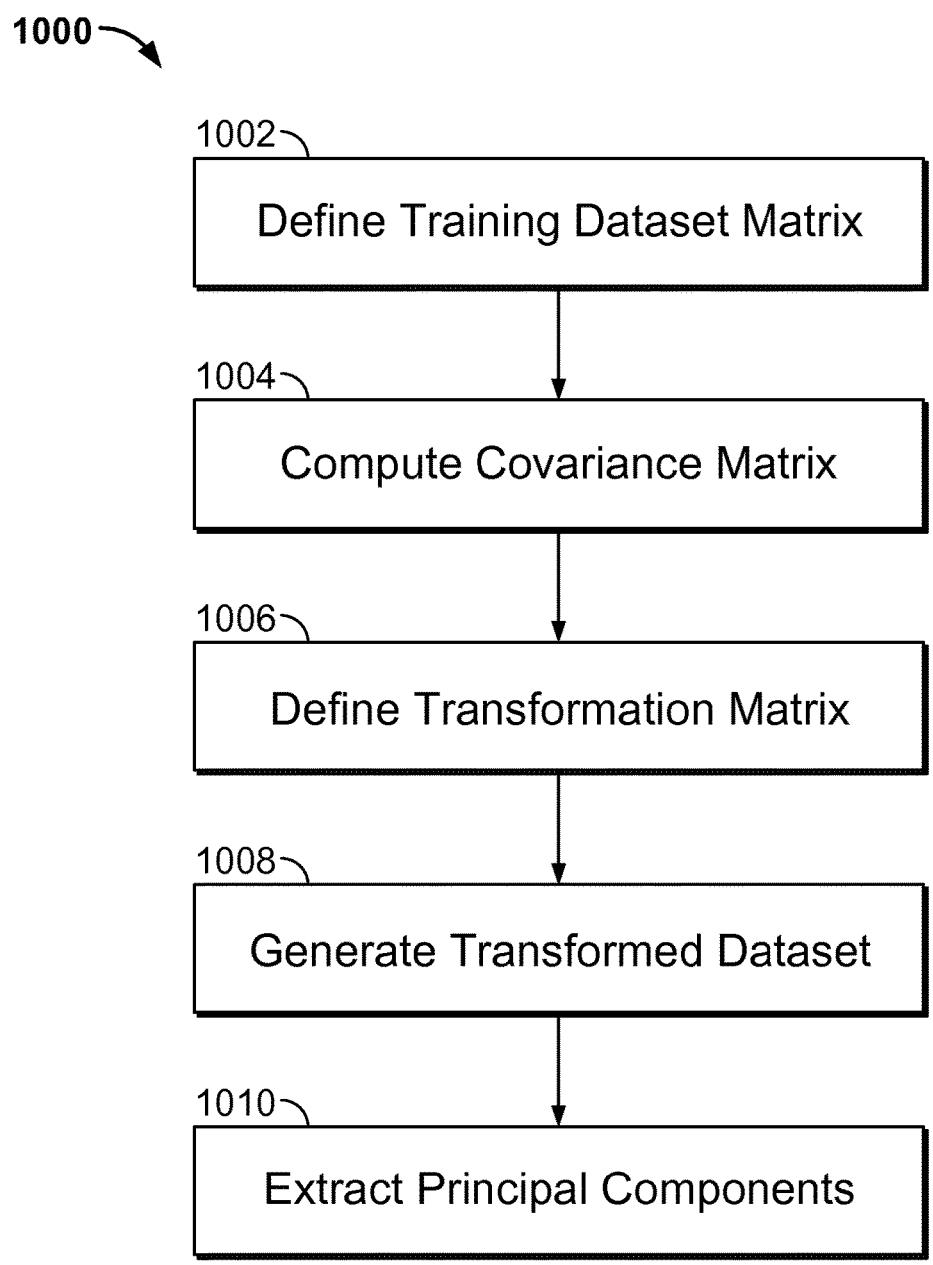
FIG. 10 is a diagram of an example principal component analysis process.

Referring to FIG. 10, an example principal component analysis process 1000 can be used to generate sets of principal components from relaxation-time distributions, where each set of principal components represents a respective one of the relaxation-time distributions. The process 1000 can include additional or different operations, and the operation can be performed in the order shown or in another order.

At 1002, a dataset matrix X is formed from the relaxation-time distributions. Each of the n relaxation-time distributions has p elements, so the dataset matrix X can be an n×p matrix (n rows, p columns), in which each of the relaxation-time distributions forms a respective row. The training dataset of relaxation-time distributions can be represented in another manner, using any suitable data format, data structure, or data type.

The relaxation-time distributions can include distributions of transverse relaxation times or longitudinal relaxation times obtained from NMR data. In some cases, the area integration of each distribution is normalized to a common normalizing value. For example, the normalizing value can be 1 or another constant value. To normalize a distribution, the values in the distribution can be multiplied or scaled uniformly so that the area of the scaled distribution is equal to the normalizing value.

At 1004, the eigenvectors of the covariance matrix C of dataset matrix X are determined. The covariance matrix C may be computed as $C=X^T X$, where $X^T$ is the transpose of the dataset matrix X, or the covariance matrix can be computed in another manner. In some instances, one or more of the eigenvectors can be obtained without explicitly computing the covariance matrix.

At 1006, a transformation matrix $W_L$ is formed, where $W_L$ is a p×l matrix whose columns are eigenvectors of the covariance matrix C. The transformation matrix $W_L$ can be formed from the l eigenvectors that correspond to the l largest eigenvalues of the covariance matrix C. The eigenvectors and eigenvalues of the covariance matrix C can be determined, for example, by conventional techniques for computing matrix eigenvectors and eigenvalues.

At 1008, the dataset matrix X is converted to a new coordinate system; the transformation generates a transformed matrix $T=XW_L$. At 1010, sets of principal components are extracted from the transformed matrix T. In some implementations, the transformed matrix T is an n×l matrix, and the $i^{th}$ row contains a set of principal components corresponding to the $i^{th}$ relaxation-time distribution in the dataset matrix X. For example, the matrix element T(i,k) (the element at the $k^{th}$ column and $i^{th}$ row), can represent the $k^{th}$ principal component of the $i^{th}$ relaxation-time distribution.

In some implementations, the data vectors in the initial coordinate system can be the $T_2$ distributions of the database obtained from NMR measurements, and each data vector can have 27 or 54 components. In some cases, the relaxation-time bins are evenly spaced along the logarithmically-scaled axis; or the bins may be spaced in another manner. After the data vectors are transformed to the new coordinate system, the first three principal components (i.e., the first three components of the transformed data vectors) or another number of transformed components can be retained for use in training (or using) the viscosity model (1010); the other 24 (or 51) components can be disregarded because they primarily represent noise or redundancy.

The same transformation can then be applied to NMR logging data extracted from another formation, for example, to predict the viscosity of fluid in the other formation. The NMR logging data can be represented as a dataset matrix $X_{input}$, and the dataset matrix $X_{input}$ can be transformed to the new coordinate system by the operation $T_{input}=X_{input}W_L$, where the transformed matrix $T_{input}$ has l columns. Here, each element $T_{input}(i,k)$ (the element at the $k^{th}$ column, $i^{th}$ row), represents the $k^{th}$ principal component of the $i^{th}$ input relaxation-time distribution, and $W_L$ represents the transformation matrix identified during model training.

Figure 11:
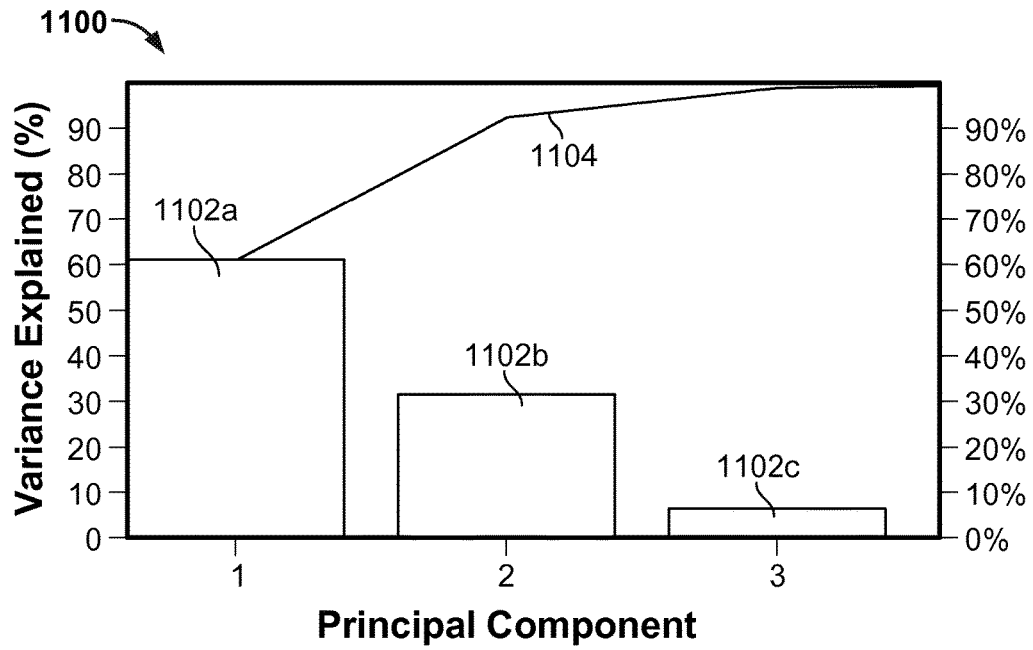
FIG. 11 is a plot that shows variance accounted for by example sets of principal components.

Referring to FIG. 11, plot 1100 shows that for an example database of $T_2$ distributions, the first three principal components 1102a-c account for over 90% of the variances (as shown by line 1104 that plots the cumulative variance after each additional principal component is added). With the understanding that lower variances represent noise or redundancy, the components having lower variances can be discarded. In some implementations, the number of retained components is determined by comparing the ratio:

$$\frac{\sum_{i=p+1}^{n} \lambda_i}{\sum_{i=1}^{n} \lambda_i}$$

with noise-to-signal ratio:

$$\frac{\sigma_{noise}^2}{\sigma_{signal}^2}$$

in the NMR measurement data, where p is the number of retained components. For example, in some implementations, NMR logging data is adequately stacked to reduce the noise to 1 pu. Assuming the average porosity is around 30 pu, the noise-to-signal ratio is about 3 percent. Thus, in this example, three principal components of the $T_2$ distribution are retained. A greater number of principal components can be retained for use in training or using the viscosity model. For example, in some implementations, four, five, six, or more principal components are retained.

In some implementations, the processed input data (e.g., the transformed matrix $T_{input}=X_{input}W_L$) can be provided as input to the RBF model, using the model coefficients identified during model training. That is, if the vector elements of $\vec{x}$ represent the processed input data, the estimated viscosity $F(\vec{x})$ can be determined by:

$$F(\vec{x}) = \sum_{i=1}^{N} \vec{w}_i \varphi(\|\vec{x}-\vec{c}_i\|),$$

where N, $\vec{w}_i$, and $\vec{c}_i$ are the model coefficients identified during model training Thus, after model training based on the principal components identified using PCA, subsequent viscosity estimates can be determined using independently acquired input NMR signals.

Figure 12:
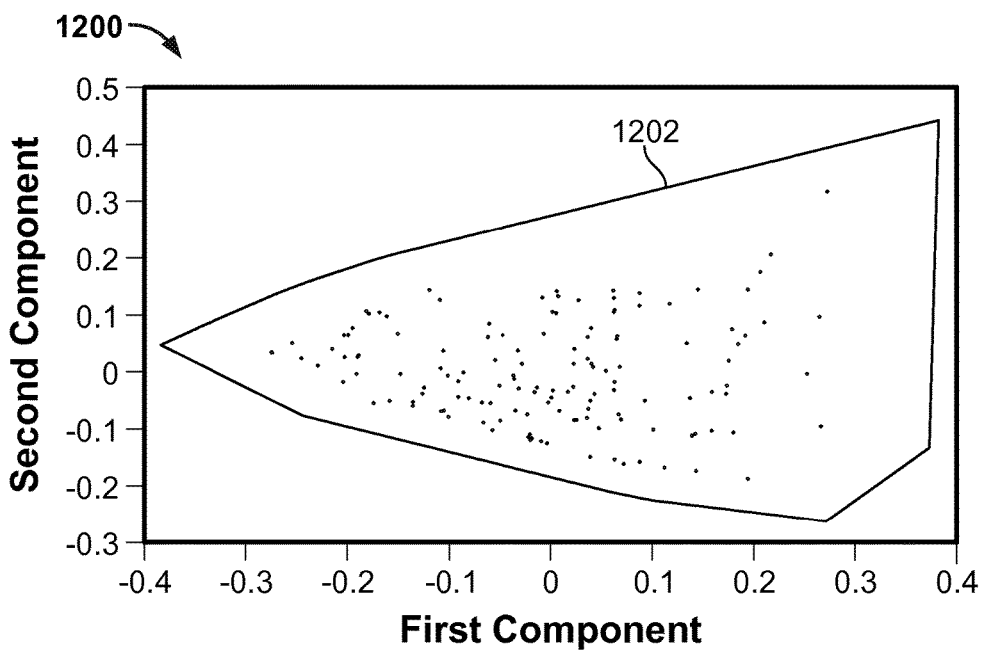
FIG. 12 is a plot that shows an example of the first two principle components of the $T_2$ distributions from the sample database and a corresponding model-application envelope.

FIG. 12 shows a plot 1200 of the first two principle components of the $T_2$ distributions from an example database. The outer polygon 1202 is the boundary for the first two components in the example database, and shows where the input parameter space of the RBF model is populated by the sample database. Because the RBF training uses interpolation, in some implementations the polygon enclosure 1202 can delineate the valid input data range where the model can yield a reliable interpolated prediction result. In some implementations, to expand this model-application envelope 1202, more data that fall outside of an existing polygon envelope 1202 can be included. In some cases, this model-application envelope 1202 can be used to generate a binary prediction reliability indicator.

In some implementations, NMR signals that are obtained ex situ are used to train the RBF model, while NMR signals obtained in situ are subsequently used to predict viscosity based on the trained RBF model. Measurements of in situ fluids are typically conducted on live oil, while measurements of ex situ fluids are typically conducted on dead oil. Live oil is subject to the higher pressures of the subterranean formation, and typically contains gas dissolved in solution. Dead oil is subject to much lower pressures (e.g., conditions at the earth's surface), and typically contains a much lower degree of gas dissolved in solution. In some instances, an RBF model can be configured to account for these and other differences between the samples used to train the RBF model and the samples that the RBF model later uses to predict viscosity. For example, an RBF model trained on dead oil can be configured to predict the viscosity of live oil.

For example, to account for such differences, a relaxation-time distribution for live oil can be mapped to its corresponding relaxation-time distribution for dead oil. Thus, an RBF model developed with dead oil samples can be used to predict the properties of live oil.

Figure 13:
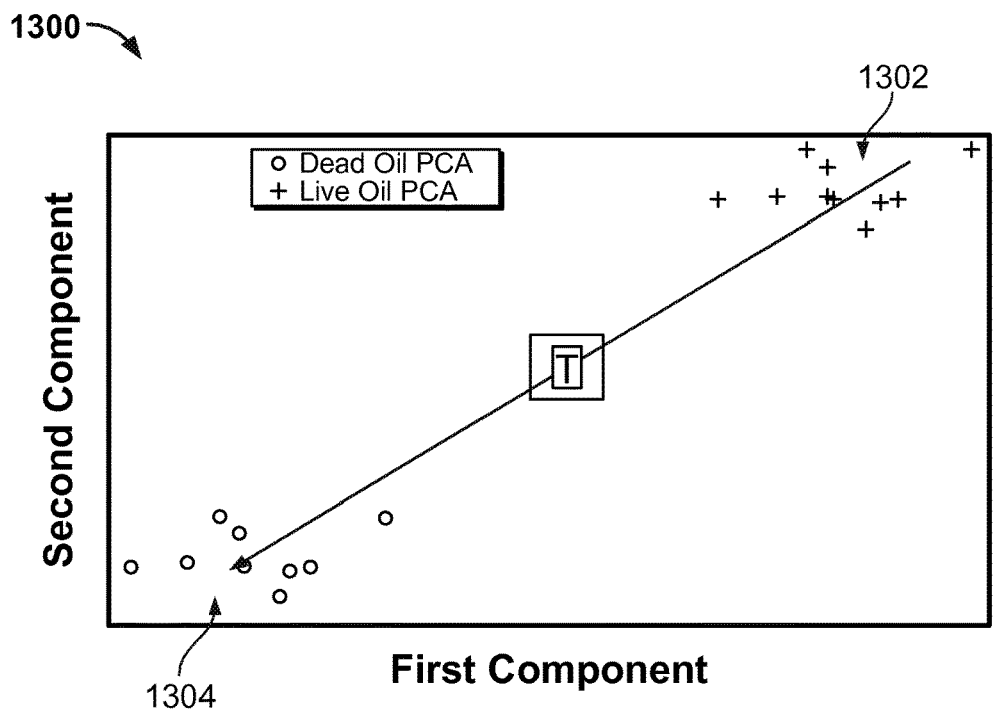
FIG. 13 is a plot that shows several example live and dead oil samples plotted according to two identified principle components.

Live oil can be correlated to dead oil in various ways. For example, in some implementations, given a number of samples of $T_2$ distributions of live oil and their corresponding $T_2$ distributions of dead oil, principle component analysis can be applied to the $T_2$ distributions of live oil and dead oil. Referring to FIG. 13, plot 1300 shows several example live oil samples 1302 and dead oil samples 1304 plotted according to two identified principle components. The transformation T from the principle components of live oil to the principle components of dead oil can be approximated with a linear transformation or nonlinear transformation. For example, if a linear transformation is used, T can be solved with a standard linear regression method. If a nonlinear transformation is used, T can be modeled as a linear combination of radial basis functions, similar to the RBF model for the correlation of viscosities and $T_2$ distributions (as discussed above). The correlation of viscosities and the $T_2$ distribution of live oil can be described as the following:

$$\eta=R(TE,HI_{app},T(X_{PCA})),$$

where $T(X_{live})$ is the transformation, T, of the principle components of a relaxation-time distribution of a live oil sample, $X_{PCA}$. Transformations can be incorporated into the RBF model as shown above or in another manner.

Figure 14:
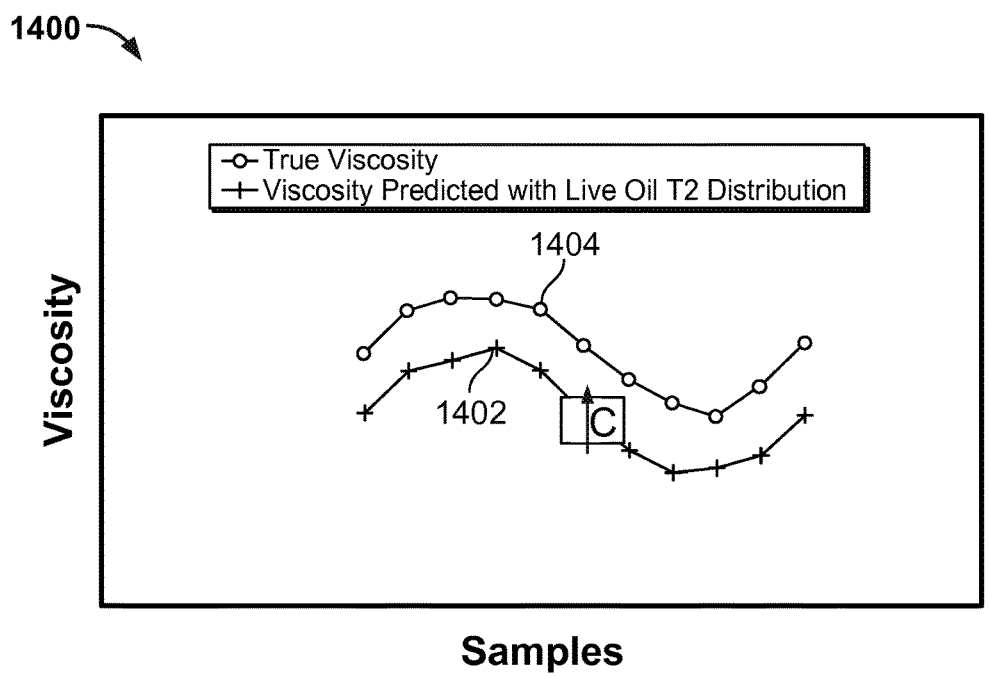
FIG. 14 is a plot that shows an example of the deviation of predictions made using an RBF model trained with $T_2$ distributions of dead oil applied to the $T_2$ distributions of live oil.

In some implementations, if the RBF model trained with the $T_2$ distributions of dead oil is applied to the $T_2$ distribution of live oil, the predicted value from the RBF model can deviate from the true value. The degree of the deviation can be modeled given a number of samples which include the $T_2$ distributions of live oil, and the true viscosities of dead oil. An example of this deviation is illustrated in plot 1400 of FIG. 14. The deviation between the predicted viscosity 1402 and the measured viscosity 1404 can be approximated with linear or nonlinear regression, and then a correction of the deviation can be inferred. For example, if C is the correction of the deviation, the correlation of viscosities and $T_2$ distribution of live oil can be described as the following:

$$\eta=C(R(TE,HI_{app},X_{PCA})),$$

where $X_{PCA}$ represents the principle components of a relaxation-time distribution of a live oil sample. Corrections can be incorporated into the RBF model as shown above or in another manner.

In the above examples, the predicted value from the RBF model is correlated to the viscosity of the dead oil. In some implementations, the RBF model predicts apparent oil viscosities based on live oil or in situ logging data, and the apparent oil viscosities may need be converted to live oil viscosities in some instances. Apparent oil viscosity can be converted into live oil viscosity in various ways. For example, in some implementations, Bergman's correlation, or many other similar empirical correlations, can be used to obtain the live oil viscosities from the apparent oil viscosities, for example, if the gas-oil ratio (GOR) of the live oil is known. In some implementations, however, these correlations are not applicable for heavy oils. In another implementation, an RBF model or a regression model can be used to convert the apparent oil viscosity to the live oil viscosity. For example, these models can be based on the live and dead oil viscosities of known samples.

Figure 15:
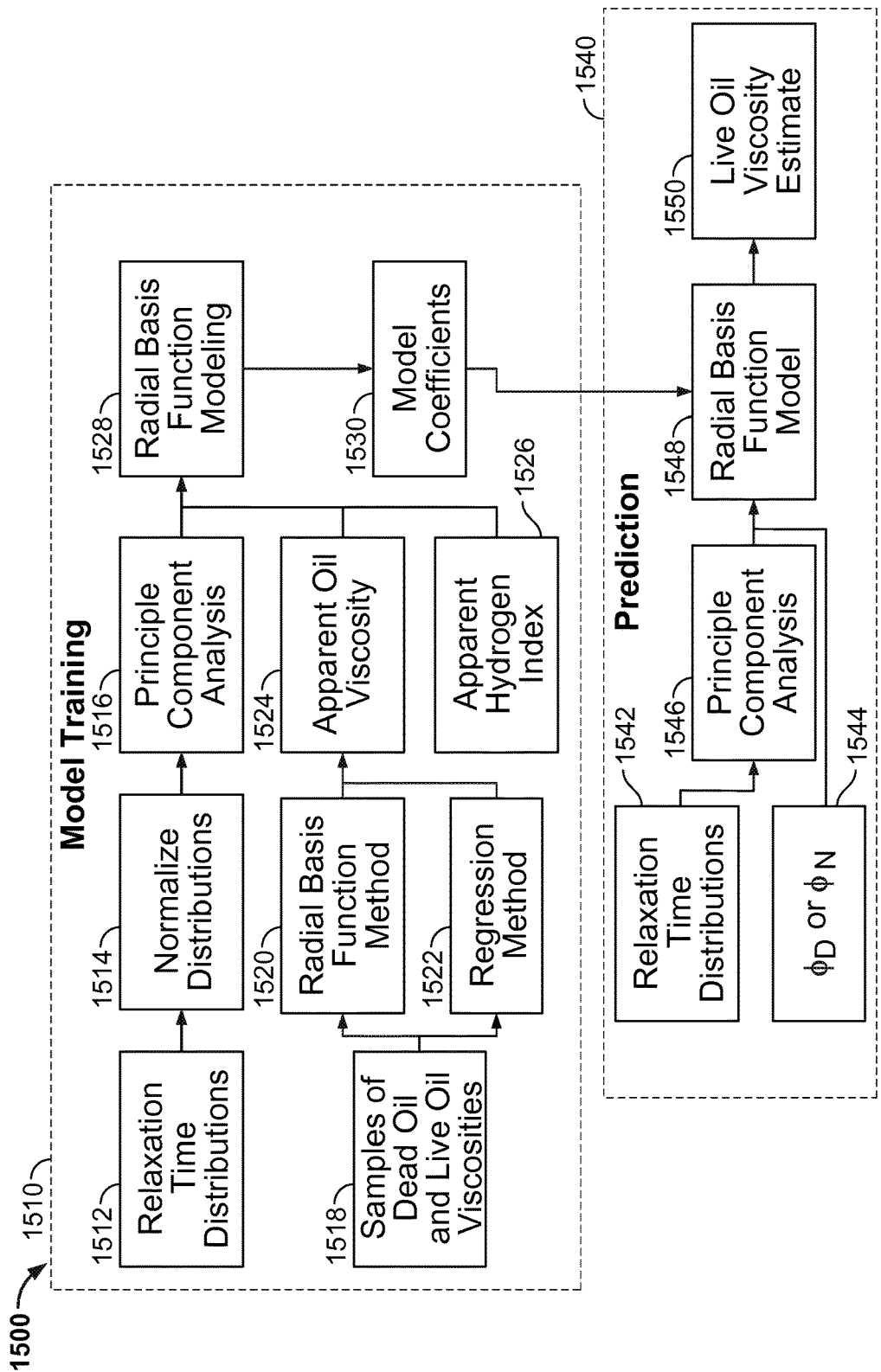
FIG. 15 is a diagram of an example process for predicting the viscosity of a subterranean formation.

Multiple techniques can be used in combination, for example, to lessen the effects of noise, account for the differences in live and dead oil, to account for over-fitting, or to otherwise improve the model. For instance, an example process 1500 for predicting the viscosity of oil from NMR measurements is shown in FIG. 15. The example process 1500 is similar in many respects to the example process 300 shown in FIG. 3.

In the example model training sub-process 1510 shown in FIG. 15, relaxation-time distributions are obtained (1512), normalized (1514), and converted to a set of principal components (1516). The principal components are used by the RBF interpolation (1528) to generate coefficients (1530). The RBF interpolation process (1528) can operate based on additional inputs, such as, for example, the apparent hydrogen index (1526), the apparent oil viscosity (1524), or a combination of these and other training data. The apparent oil viscosity can be obtained from measured viscosities of dead oil and live oil (1518), for example, based on a regression method (1522), an RBF method (1520), or a combination of these and others.

In the example viscosity prediction sub-process 1540 shown in FIG. 15, the input relaxation-time distributions (1542) are normalized and converted to a set of principal components (1546). In some cases, each distribution is normalized to the same normalizing value that was used at 1514 in the model training sub-process 1510; and the principal components are obtained by applying the same transformation that was used at 1516 in the model training sub-process 1510. The bulk density or neutron density or both can be used for the apparent hydrogen indices (1544), in some instances. The principal components are provided as input to the radial basis function model 1548, and the resulting viscosity for live oil (1550) can be used to predict viscosity values in situ.

Figure 16:
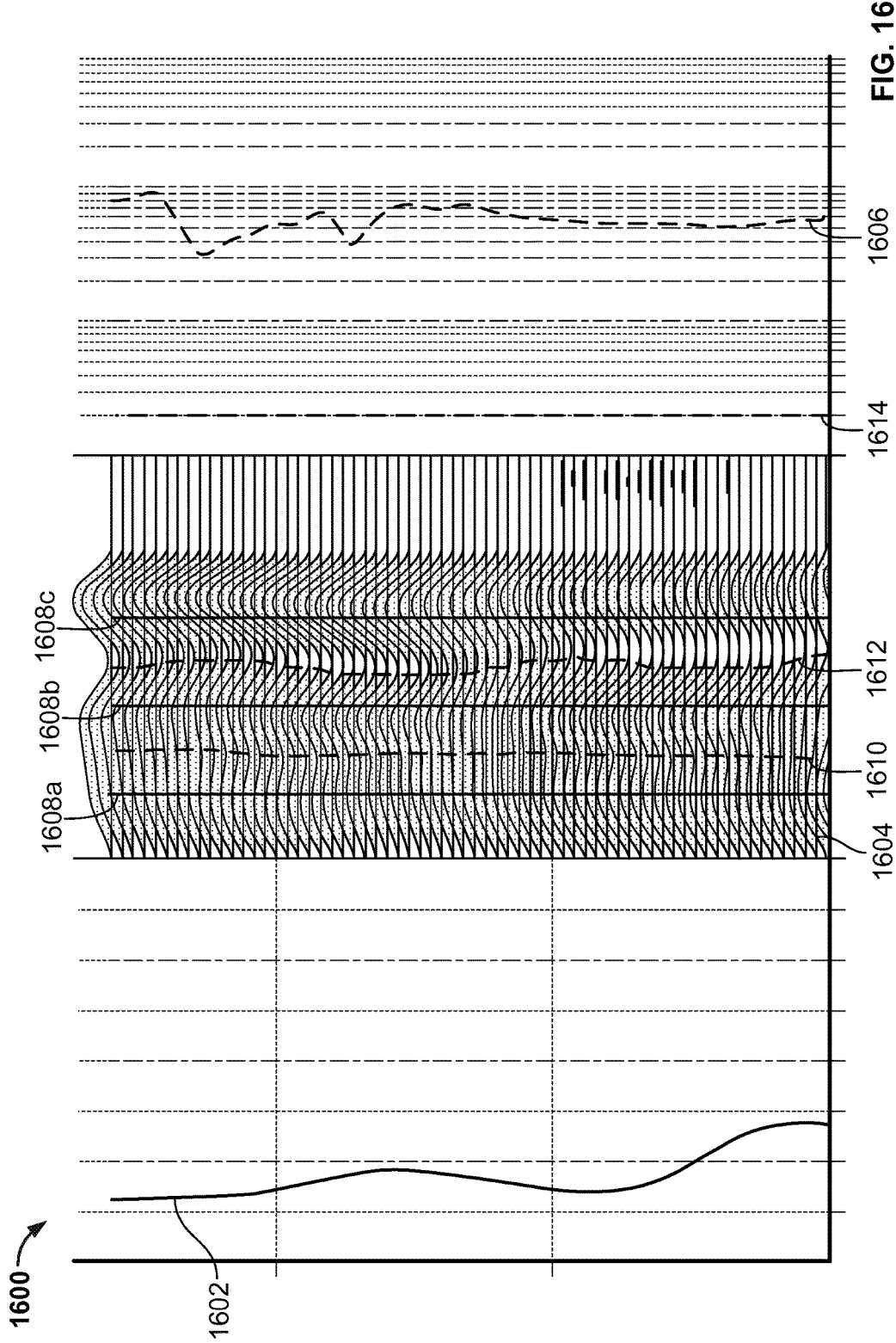
FIG. 16 includes plots that show the application of an example process for predicting the viscosity of subterranean fluid.

FIG. 16 shows example data from applying the example process 1500 shown in FIG. 15. In the plot 1600, the left curve 1602 shows the total porosities from the NMR measurement, the set of curves 1604 in the middle panel shows the $T_2$ distributions, and the third curve 1606 shows the viscosities predicted by the RBF model. In the middle panel, the three solid lines 1608a-c are indicators for 1 ms, 10 ms, and 100 ms of the $T_2$ distributions, respectively. In the example shown, the left dashed line 1610 is the cut-off of the oil signals, and the right dashed line 1612 is the $T_2$ geometric mean of the oil. The dashed line 1614 provides an indicator of reliability of the prediction; in this example, the indicator shows that the predictions are reliable. In some implementations, the dashed line 1614 can represent a binary indicator for reliability. In some examples, predictions outside the dashed line 1614 can be considered unreliable, while predictions inside the dashed line 1614 can be considered reliable.

This example process 1500 allows for the prediction of oil viscosity in situ, based on training data obtained either in situ or ex situ. Process 1500 is one example of how the above-described techniques can be employed in combination to enhance the predictive accuracy of the RBF model. Other combinations of the above techniques can be used.

Some embodiments of subject matter and operations described in this specification can be implemented in digital electronic circuitry, or in computer software, firmware, or hardware, including the structures disclosed in this specification and their structural equivalents, or in combinations of one or more of them. Some embodiments of subject matter described in this specification can be implemented as one or more computer programs, i.e., one or more modules of computer program instructions encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, or distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback, and input from the user can be received in any form, including acoustic, speech, or tactile input. In addition, a computer can interact with a user by sending documents to and receiving documents from a device that is used by the user, for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 17:
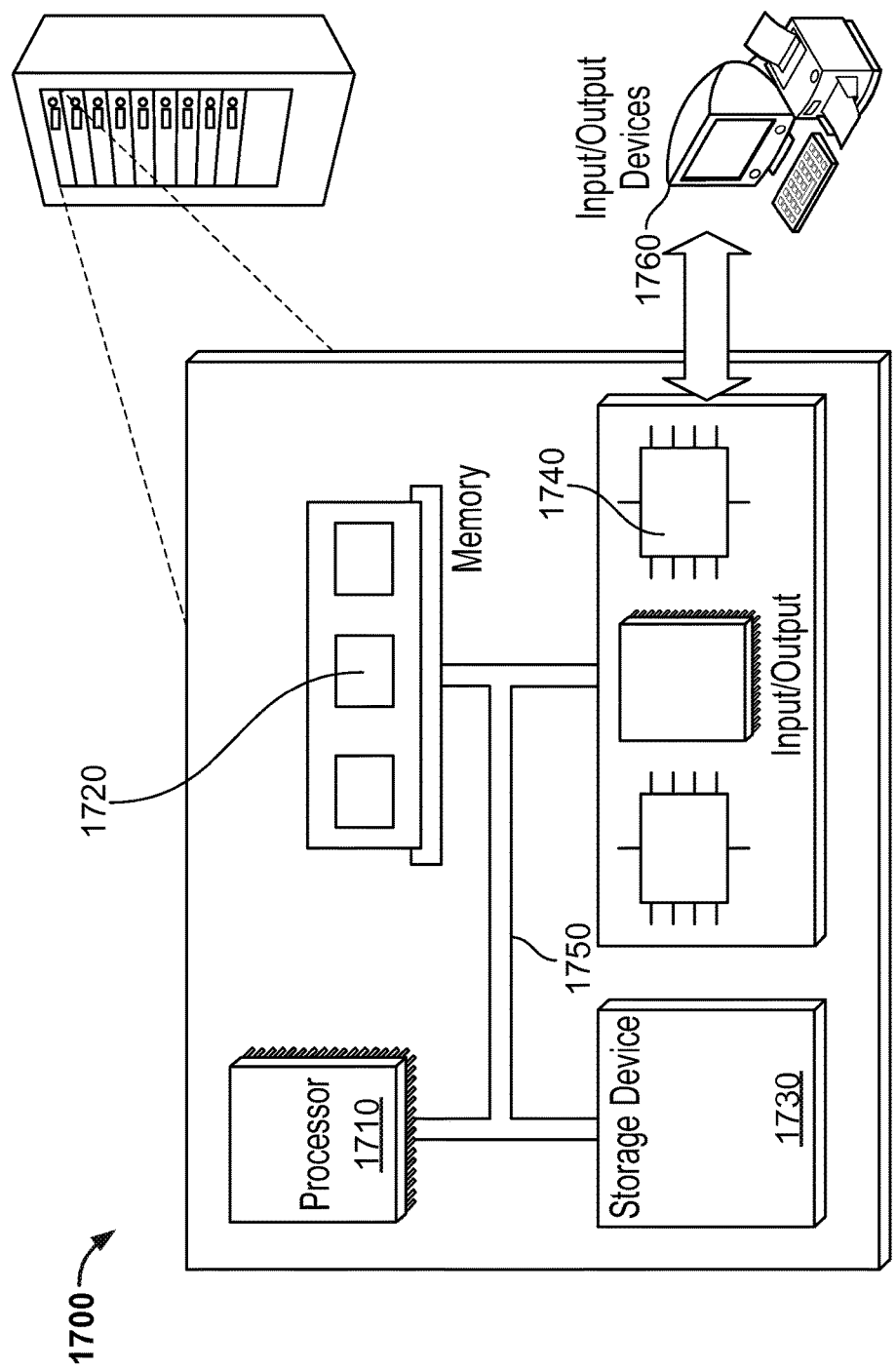
FIG. 17 shows a diagram of an example computer system.

FIG. 17 shows an example computer system 1700. The system 1700 includes a processor 1710, a memory 1720, a storage device 1730, and an input/output device 1740. Each of the components 1710, 1720, 1730, and 1740 can be interconnected, for example, using a system bus 1750. The processor 1710 is capable of processing instructions for execution within the system 1700. In some implementations, the processor 1710 is a single-threaded processor, a multi-threaded processor, or another type of processor. The processor 1710 is capable of processing instructions stored in the memory 1720 or on the storage device 1730. The memory 1720 and the storage device 1730 can store information within the system 1700.

The input/output device 1740 provides input/output operations for the system 1700. In some implementations, the input/output device 1740 can include one or more network interface devices, e.g., an Ethernet card, a serial communication device, e.g., an RS-232 port, and/or a wireless interface device, e.g., an 802.11 card, a 3G wireless modem, a 4G wireless modem, etc. In some implementations, the input/output device can include driver devices configured to receive input data and send output data to other input/output devices, e.g., keyboard, printer and display devices 1760. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

A number of examples have been described. Nevertheless, it will be understood that various modifications can be made. Accordingly, other implementations are within the scope of the following claims.

The invention claimed is:

1. A method of training a subterranean heavy oil viscosity model based on nuclear magnetic resonance (NMR) data, the method comprising steps:
    (a) conducting multiple ex-situ NMR measurements consisting of individual Carr Purcell Meiboom Gill (CPMG) echo trains corresponding to different inter-echo spacing values (TE) from a sample collected from a subterranean region;
    (b) obtaining individual relaxation-time distributions corresponding to the individual TE values in step (a);
    (c) normalizing each relaxation-time distribution to a common normalizing value to obtain a normalized relaxation-time distribution whose integral equals the common normalizing value;
    (d) repeating steps (a)-(c) with multiple heavy oil samples from different subterranean regions having different viscosities;
    (e) obtaining oil viscosity values of all samples with a non-NMR means;
    (f) producing a subterranean fluid viscosity model for heavy oil by computing parameters for a plurality of weighted radial basis functions from the normalized relaxation-time distributions and the viscosity values from step (e); and
    (g) determining properties of hydrocarbon fluid in the subterranean region based only on the NMR data using the viscosity model in step (f) for use in reservoir quality assessment and, based on the determined properties, selection of which wells and/or which depth interval of a well to move into production.

2. The method of claim 1, wherein the parameters are computed based on multiple sets of principal components from the normalized relaxation-time distributions, and the method further comprises generating the multiple sets of principal components from the normalized relaxation-time distributions.

3. The method of claim 1, wherein computing the parameters comprises using a cost function to reduce a magnitude of variation among weighting parameters of the weighted radial basis functions.

4. The method of claim 1, comprising:
    accessing fluid viscosity measurements obtained from core samples or reservoir fluid samples extracted from the subterranean region; and
    computing the parameters based on the viscosity measurements and the normalized relaxation-time distributions.

5. The method of claim 1, comprising:
    accessing an inter-echo time associated with each relaxation-time distribution; and
    computing:
        the parameters from the normalized relaxation-time distributions, and
        an apparent hydrogen index associated with each relaxation-time distribution.

6. The method of claim 1, further comprising generating the relaxation-time distributions from NMR datasets, where each NMR dataset is associated with a respective inter-echo time, and at least two of the NMR datasets are associated with different echo times.

7. The method of claim 1, comprising producing a subterranean heavy oil viscosity model that is adapted to predict viscosity based on relaxation-time distributions produced from an NMR dataset having any one inter-echo time.

8. The method of claim 1, wherein the relaxation-time distributions are generated from NMR measurements of heavy oil in a core sample or reservoir fluid sample extracted from the subterranean region, and the method further comprises:
    determining a transformation that converts principal components of relaxation-time distributions generated from NMR measurements of live oil to corresponding principal components of relaxation-time distributions generated from NMR measurements of heavy oil; and
    including the transformation in the subterranean heavy oil viscosity model.

9. The method of claim 1, wherein the relaxation-time distributions are generated from NMR measurements of heavy oil in a core sample or reservoir fluid sample extracted from the subterranean region, and the method further comprises:
    determining a correction that converts viscosity values obtained based on NMR measurements of live oil to corresponding viscosity values based on NMR measurements of heavy oil; and
    including the correction in the subterranean heavy oil viscosity model.

10. A system comprising:
a nuclear magnetic resonance (NMR) measurement system adapted to acquire NMR measurements of heavy oil associated with a subterranean region; and
a computing system comprising:
 a communication interface operable to receive the NMR measurements; and
 a data processing apparatus operable to perform operations comprising steps:
  (a) conducting multiple ex-situ measurements consisting of individual Carr Purcell Meiboom Gill (CPMG) echo trains corresponding to different inter-echo spacing (TE) values from a sample collected from subterranean region;
  (b) obtaining individual relaxation-time distributions corresponding to the individual TE values in step (a);
  (c) normalizing each relaxation-time distribution to a common normalizing value to obtain a normalized relaxation-time distribution whose integral equals the common normalizing value;
  (d) repeating steps (a)-(c) with multiple heavy oil samples from different subterranean regions having different viscosities;
  (e) obtaining oil viscosity values of all samples with a non-NMR means;
  (f) producing a subterranean fluid viscosity model for heavy oil by computing parameters for a plurality of weighted radial basis functions from the normalized relaxation-time distributions and the viscosity values from step (e); and
  (g) determining properties of hydrocarbon fluid in the subterranean region based only on the NMR data using the viscosity model in step (f) for use in reservoir quality assessment and, based on the determined properties, selection of which wells or which depth interval in a well to move into production.

11. The system of claim 10, wherein the NMR measurement system comprises a laboratory NMR system that acquires the NMR measurements from core samples or reservoir fluid samples extracted from the subterranean region.

12. The system of claim 10, wherein the parameters are computed based on multiple sets of principal components from the normalized relaxation-time distributions, and wherein the operations comprise generating the multiple sets of principal components from the normalized relaxation-time distributions.

13. The system of claim 10, wherein computing the parameters comprises using a cost function to reduce a magnitude of variation among weighting parameters of the weighted radial basis functions.

14. The system of claim 10, wherein the operations further comprise:
accessing an inter-echo time associated with each relaxation-time distribution; and
computing:
 the parameters from the normalized relaxation-time distributions, and
 an apparent hydrogen index associated with each relaxation-time distribution.

15. The system of claim 10, wherein the NMR measurement system comprises a laboratory NMR system that acquires the NMR measurements from heavy oil in a core sample or reservoir fluid sample extracted from the subterranean region, and the operations further comprise:
determining a transformation that converts principal components of relaxation-time distributions generated from NMR measurements of live oil to corresponding principal components of relaxation-time distributions generated from NMR measurements of heavy oil; and
including the transformation in the subterranean heavy oil viscosity model.

16. The system of claim 10, wherein the NMR measurement system comprises a laboratory NMR system that acquires the NMR measurements from heavy oil in a core sample or reservoir fluid sample extracted from the subterranean region, and the operations further comprise:
determining a correction that converts viscosity values obtained based on NMR measurements of live oil to corresponding viscosity values based on NMR measurements of heavy oil; and
including the correction in the subterranean heavy oil viscosity model.

17. A non-transitory computer readable medium storing instructions that are operable when executed by data processing apparatus to perform operations comprising steps:
 (a) conducting multiple ex-situ nuclear magnetic resonance (NMR) measurements consisting of individual Carr Purcell Meibomm Gill (CPMG) echo trains corresponding to different inter-echo spacing (TE) values from a sample collected from a subterranean region;
 (b) obtaining individual relaxation-time distributions corresponding to the individual TE values in step (a);
 (c) normalizing each relaxation-time distribution to a common normalizing value to obtain a normalized relaxation-time distribution whose integral equals the common normalizing value;
 (d) repeating steps (a)-(c) with multiple heavy oil samples from different subterranean regions having different viscosities;
 (e) obtaining oil viscosity values of all samples with a non-NMR means;
 (f) producing a subterranean fluid viscosity model for heavy oil by computing parameters for a plurality of weighted radial basis functions from the normalized relaxation-time distributions and the viscosity values from step (e); and
 (g) determining properties of hydrocarbon fluid in the subterranean region based only on the NMR data using the viscosity model in step (f) for use in reservoir quality assessment and, based on the determined properties, selection of which wells and/or which depth interval of a well to move into production.

18. The computer readable medium of claim 17, wherein the parameters are computed based on multiple sets of principal components from the normalized relaxation-time distributions, and the operations comprise generating the multiple sets of principal components from the normalized relaxation-time distributions.

19. The computer readable medium of claim 17, wherein computing the parameters includes using a cost function to reduce a magnitude of variation among weighting parameters of the weighted radial basis functions.

20. The computer readable medium of claim 17, the operations comprising:
accessing an inter-echo time associated with each relaxation-time distribution; and
computing:
 the parameters from the normalized relaxation-time distributions, and
 an apparent hydrogen index associated with each relaxation-time distribution.

21. The computer readable medium of claim 17, the operations comprising generating the relaxation-time distributions from NMR datasets, where each NMR dataset is associated with a respective echo time, and at least two of the NMR datasets are associated with different echo times.

22. The computer readable medium of claim 17, the operations comprising producing a subterranean heavy oil viscosity model that is adapted to predict viscosity based on relaxation-time distributions produced from an NMR dataset having any one inter-echo time.

* * * * *